United States Patent
Atsumi et al.

(10) Patent No.: US 10,184,138 B2
(45) Date of Patent: Jan. 22, 2019

(54) BACTERIA ENGINEERED FOR CONVERSION OF ETHYLENE TO ETHANOL

(71) Applicant: The Regents of the University of California, Oakland, CA (US)

(72) Inventors: Shota Atsumi, Davis, CA (US); Michael D. Toney, Davis, CA (US); Gabriel M. Rodriguez, Davis, CA (US); Yohei Tashiro, Davis, CA (US); Justin B. Siegel, Davis, CA (US); D. Alexander Carlin, Davis, CA (US); Irina Koryakina, Davis, CA (US); Shuchi H. Desai, Davis, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 15/317,656

(22) PCT Filed: Jun. 9, 2015

(86) PCT No.: PCT/US2015/034942
§ 371 (c)(1),
(2) Date: Dec. 9, 2016

(87) PCT Pub. No.: WO2015/191611
PCT Pub. Date: Dec. 17, 2015

(65) Prior Publication Data
US 2017/0137846 A1  May 18, 2017

Related U.S. Application Data

(60) Provisional application No. 62/009,857, filed on Jun. 9, 2014.

(51) Int. Cl.
| | | |
|---|---|---|
| C12N 1/20 | (2006.01) | |
| C12P 7/06 | (2006.01) | |
| C12N 9/02 | (2006.01) | |
| C12N 9/88 | (2006.01) | |
| C12P 7/16 | (2006.01) | |
| C12N 15/52 | (2006.01) | |

(52) U.S. Cl.
CPC .............. *C12P 7/06* (2013.01); *C12N 9/0008* (2013.01); *C12N 9/0073* (2013.01); *C12N 9/88* (2013.01); *C12N 15/52* (2013.01); *C12P 7/16* (2013.01); *C12Y 101/01157* (2013.01); *C12Y 102/01002* (2013.01); *C12Y 102/01003* (2013.01); *C12Y 103/01038* (2013.01); *C12Y 114/13* (2013.01); *C12Y 114/13069* (2013.01); *C12Y 203/01009* (2013.01); *C12Y 402/01* (2013.01); *C12Y 402/01053* (2013.01); *C12Y 402/01095* (2013.01); *Y02E 50/10* (2013.01); *Y02E 50/17* (2013.01)

(58) Field of Classification Search
CPC .............. C12N 15/63; C12N 9/02; C12P 7/06

USPC ....................................................... 435/252.3
See application file for complete search history.

(56) References Cited

U.S. PATENT DOCUMENTS

| | | | |
|---|---|---|---|
| 5,028,539 A | 7/1991 | Ingram et al. | |
| 5,536,659 A | 7/1996 | Fukuda et al. | |
| 2010/0068775 A1* | 3/2010 | Achkar ..................... | C12P 7/22 |
| | | | 435/156 |
| 2010/0068776 A1 | 3/2010 | Woods et al. | |
| 2014/0065697 A1 | 3/2014 | Zhang et al. | |

FOREIGN PATENT DOCUMENTS

| | | |
|---|---|---|
| WO | 2011/076689 A1 | 6/2011 |
| WO | 2011/076691 A1 | 6/2011 |
| WO | 2014/037328 A1 | 3/2014 |
| WO | 2015/191611 A1 | 12/2015 |

OTHER PUBLICATIONS

Smith et al. Eur. J. Biochem. 260, 446-452 (1999).*
Atsumi et al., "Metabolic Engineering of *Escherichia coli* for 1-Butanol Production", Metabolic Engineering, vol. 10, No. 6, 2008, pp. 305-311.
Bevers et al., "Oleate Hydratase Catalyzes the Hydration of a Nonactivated Carbon-Carbon Bond", Journal of Bacteriology, vol. 191, No. 15, Aug. 2009, pp. 5010-5012.
Carlin et al., "Biocatalytic Conversion of Ethylene to Ethylene Oxide using an Engineered Toluene Monooxygenase", Chem. Commun., vol. 51, 2015, pp. 2283-2285.
Desai et al., "Biological Conversion of Gaseous Alkenes to Liquid Chemicals", Metabolic Engineering, vol. 38, 2016, pp. 98-104.
International Preliminary Report on Patentability received for PCT Patent Application No. PCT/US2015/034942, dated Dec. 22, 2016, 11 pages.
International Search Report and Written Opinion received for PCT Patent Application No. PCT/US2015/034942, dated Nov. 23, 2015, 15 pages.
Invitation to Pay Additional Fees received for PCT Patent Application No. PCT/US2015/034942, dated Sep. 10, 2015, 3 pages.
Mowafy et al., "2-Haloacrylate Hydratase, a New Class of Flavoenzyme that Catalyzes the Addition of Water to the Substrate for Dehalogenation" Applied and Environmental Microbiology, vol. 76, No. 18, Sep. 2010, pp. 6032-6037.

(Continued)

*Primary Examiner* — Tekchand Saidha
(74) *Attorney, Agent, or Firm* — Morrison & Foerster LLP

(57) ABSTRACT

The present disclosure provides recombinant bacteria with elevated production of ethanol and/or n-butanol from ethylene. Methods for the production of the recombinant bacteria, as well as for use thereof for production of ethanol and/or n-butanol are also provided.

15 Claims, 8 Drawing Sheets

(56) References Cited

OTHER PUBLICATIONS

Aasberg-Petersen et al., "Large Scale Methanol Production from Natural Gas", Haldor Topsoe, 2008, pp. 1-14.
Shen et al., "Driving Forces Enable High-Titer Anaerobic 1-Butanol Synthesis in *Escherichia coli*", Applied and Environmental Microbiology, vol. 77, No. 9, May 2011, pp. 2905-2915.

* cited by examiner

Ethylene to n-butanol

BACTERIA ENGINEERED FOR CONVERSION OF ETHYLENE TO ETHANOL

CROSS-REFERENCE TO RELATED APPLICATIONS

This application is a U.S. National Phase patent application of PCT/US2015/034942, filed Jun. 9, 2015, which claims the benefit of U.S. Provisional Application No. 62/009,857, filed Jun. 9, 2014, the disclosures of which are herein incorporated by reference in their entirety.

STATEMENT OF GOVERNMENT SUPPORT

This invention was made with Government support under Grant No. DE-AR0000429 awarded by the Department of Energy. The Government has certain rights in this invention.

FIELD

The present disclosure provides recombinant bacteria with elevated production of ethanol and/or n-butanol from ethylene. Methods for the production of the recombinant bacteria, as well as for use thereof for production of ethanol and/or n-butanol are also provided.

BACKGROUND

In the midst of declining fossil fuels reserves and a great expansion of natural gas production, increasing effort is seeking to commercialize the conversion of methane into chemical feedstocks and fuels as an alternative to petroleum. Large natural gas reservoirs exist throughout the world and, thus, have an enormous potential as a clean fuel and chemical feedstock. Currently, the vast majority of natural gas is used for heating purposes. This is due largely to the properties of methane as a heating fuel as well as the difficulty in economically converting methane into larger, higher value chemicals and liquid fuels.

Several methods to convert methane indirectly and directly into higher olefins have been report in literature. However, the two large-scale methods being used commercially are methanol-to-olefins (MTO) and the Fischer-Tropsch synthesis (FT) (Alvarez-Galvan et al., Catalysis Today 171, 15-23, 2011). Both these processes first involve the generation of synthesis gas (Syngas), a mixture of $H_2$ and CO (Alvarez-Galvan, supra, 2011). Syngas production is energy intense, requiring high temperatures (>600° C.), making it a costly process that typically represents 60% of total capital costs (Aasberg-Petersen et al., available at: www.topsoe.com/business_areas/methanol/~/media/PDF%20files/Methanol/Topsoe_large_scale_methanol_prod-_paper.ashx, 2008). Thus, direct routes for conversion of methane to olefins and other chemicals are conceptually preferable and many methods have been reported (Alvarez-Galvan et al., supra, 2011). However, these reported methods suffer from low yield and low product specificity rendering them uneconomical thus far. Therefore, a need exists for a novel, more cost effective route to produce chemical feedstocks and fuels from methane.

The challenges in the overall conversion of methane to chemicals, either directly or indirectly, largely stem from the activation energy required to convert methane into large molecules. This is a result of stability and symmetry of methane. Current solutions to activate methane involve the use of inorganic catalysts such as palladium, which serve to reduce the energy required for methane activation (Aasberg-Petersen et al., supra, 2008). The use of high temperatures and pressures are also needed. These processes are extremely energy intense and also lack product specificity, requiring additional purification steps to separate the various products.

To circumvent these pitfalls, described herein are biosynthetic pathways for the conversion of ethylene, which may be converted from methane with established methods, to acetyl-CoA. The biological assimilation of ethylene has only been reported in methanotrophs (Bull et al., Nature 405, 175-178, 2000; and Treude et al., Appl Environ Microbiol 73, 2271-2283, 2007). Due to the difficulties in culturing methanotrophs and very few genetic modification tools, no large-scale applications of these organisms has been demonstrated. Therefore, the present disclosure describes the construction of ethylene assimilation pathway in recombinant bacteria, which already have a plethora of available genetic tools and has well-established large-scale applications. Furthermore, several examples of pathways for converting basic metabolites to fuels and chemicals (e.g., acetyl-CoA to n-butanol) in *E. coli* have been extensively reported (Rabinovitch-Deere et al., Chemical reviews 113, 4611-32, 2013). Thus, by engineering a high flux ethylene assimilation pathway in recombinant bacteria, better performance may be achieved than what has been demonstrated in methanotrophs.

Lastly, since ethylene is already a high volume chemical feedstock used in the chemical industry, a high performance ethylene assimilation pathway in recombinant bacteria could enable immediate industrial applications. Due to the broad uses of ethylene as a chemical feedstock, technological innovations for the conversion of methane to ethylene will be developed. Therefore, a well-engineered ethylene assimilation pathway in a user-friendly host such as recombinant bacteria will enable the biological conversion of ethylene into liquid fuels and other high value chemicals.

SUMMARY

The present disclosure provides recombinant bacteria with elevated production of ethanol and/or n-butanol from ethylene. Methods for the production of the recombinant bacteria, as well as for use thereof for production of ethanol and/or n-butanol are also provided.

In particular, the present disclosure provides bacteria comprising a recombinant polynucleotide encoding an ethylene hydratase (EH), wherein expression of the EH results in an increase in production of ethanol as compared to a corresponding bacterium (e.g., same genus and species) lacking the recombinant polynucleotide. In some embodiments, the EH is an oleate hydratase. In certain embodiments, the oleate hydratase is a *Lysinibacillus fusiformis* oleate hydratase. In some embodiments, the EH is a 2-haloacrylate hydratase. In certain embodiments, the 2-haloacrylate hydratase is a *Pseudomonas* species 2-haloacrylate hydratase. In some embodiments, the EH is a kievitone hydratase. In certain embodiments, the kievitone hydratase is a *Fusarium solani* kievitone hydratase. The present disclosure further provides bacteria comprising a recombinant polynucleotide encoding an alkene monooxygenase (AMO) and an ethylene oxide reductase (EOR), wherein expression of the AMO and the EOR results in an increase in production of ethanol as compared to a corresponding bacterium (e.g., same genus and species) lacking the recombinant polynucleotide. In some embodiments, the AMO is a toluene monooxygenase. In certain embodiments, the toluene monooxygenase is a *Pseudomonas mendocina* toluene monooxygenase. In certain embodiments, the toluene monooxygenase is a *Burkholderia cepacia* toluene monooxygenase. In some embodiments, the EOR is an NAD+ dependent formate dehydrogenase. In some embodiments, the recombinant polynucleotide comprises a first polynucleotide encoding the alkene monooxygenase (AMO) and a second polynucleotide encoding the ethylene oxide reductase (EOR). In some embodiments that may be combined with any of the preceding embodiments, the bacterium further comprises a further recombinant polynucleotide encoding an alcohol/aldehyde dehydrogenase (AADH), wherein expression of either the EH, or the AMO and the EOR, in combination with the AADH results in an increase in production of acetyl-CoA as compared to a corresponding bacterium (e.g., same genus and species) lacking the recombinant polynucleotides. In certain embodiments, the AADH is an *E. coli* AdhE. In some embodiments that may be combined with any of the preceding embodiments, the bacterium further comprises a further recombinant polynucleotide encoding an ethanol dehydrogenase (EDH), wherein expression of either the EH, or the AMO and the EOR, in combination with the EDH results in an increase in production of an acetaldehyde as compared to a corresponding bacterium (e.g., same genus and species) lacking the recombinant polynucleotides. In certain embodiments, the EDH is an *E. coli* AdhP. In some embodiments, the bacterium further comprises a still further recombinant polynucleotide encoding an acetoaldehyde dehydrogenase (ALDH), wherein expression of either the EH, or the AMO and the EOR, in combination with the EDH and the ALDH results in an increase in production of acetyl-CoA as compared to a corresponding bacterium (e.g., same genus and species) lacking the recombinant polynucleotides. In certain embodiments, the ALDH is an *E. coli* MhpF. In certain embodiments, the ALDH is a *Listeria monocytogenes* EdgE. In certain embodiments, the EDH is an *E. coli* AdhP. The present disclosure further provides bacteria comprising a recombinant polynucleotide encoding an alkene monooxygenase (AMO) and an epoxide hydrolase (EPH), wherein expression of the AMO and the EPH results in an increase in production of ethylene glycol as compared to a corresponding bacterium (e.g., same genus and species) lacking the recombinant polynucleotide. In some embodiments, the bacterium further comprises a further recombinant polynucleotide encoding a glycoaldehyde reductase (GR), wherein expression of the AMO, the EPH, and the GR results in an increase in production of glycoaldehyde as compared to a corresponding bacterium (e.g., same genus and species) lacking the recombinant polynucleotides. In some embodiments, the bacterium further comprises a still further recombinant polynucleotide encoding a phosphoketolase (PK), wherein expression of the AMO, the EPH, the GR, and the PK results in an increase in production of acetyl-phosphate as compared to a corresponding bacterium (e.g., same genus and species) lacking the recombinant polynucleotides. In some embodiments, the bacterium further comprises a yet further recombinant polynucleotide encoding a phosphate acetyltransferase (PA), wherein expression of the AMO, the EPH, the GR, the PK, and the PA results in an increase in production of acetyl-CoA as compared to a corresponding bacterium (e.g., same genus and species) lacking the recombinant polynucleotides. In some embodiments, the bacterium further comprises a yet still further recombinant polynucleotides encoding an acetoacetyl-CoA thiolase (AT), a 3-hydroxybutyryl-CoA dehydrogenase (HBD), a crotonase (CRT), a trans-enoyl-CoA reductase (TER), and an alcohol/aldehyde dehydrogenase (AADH), wherein expression of the AT, the HBD, the CRT, the TER, and the AADH results in an increase in production of n-butanol as compared to a corresponding bacterium (e.g., same genus and species) lacking the recombinant polynucleotides. In certain embodiments, the AT is an *E. coli* AtoB. In certain embodiments, the HBD is a *C. acetobutylicum* Hbd. In certain embodiments, the CRT is a *C. acetobutylicum* Crt. In certain embodiments, the TER is a *T. denticola* Ter. In certain embodiments, the AADH is a *Clostridium acetobutylicum* AdhE2. In some embodiments that may be combined with any of the preceding embodiments, at least one of the recombinant polynucleotides is stably integrated into the genome of the bacterium. In some embodiments that may be combined with any of the preceding embodiments, the bacterium is *E. coli*.

In addition, the disclosure provides methods for producing ethanol. The methods include: a) providing the bacteria as described in the preceding paragraph; and b) culturing the bacteria of (a) in culture medium comprising a substrate under conditions suitable for the conversion of the substrate to ethanol, wherein expression of either the EH, or the AMO and the EOR, results in an increase in production of ethanol as compared to a corresponding bacterium (e.g., same genus and species) lacking the recombinant polynucleotide(s), when cultured under the same conditions. In some embodiments, the methods further include substantially purifying the ethanol. In addition, the disclosure provides methods for producing n-butanol. The methods include: a) providing the bacteria as described in the preceding paragraph; and b) culturing the bacterium of (a) in culture medium comprising a substrate under conditions suitable for the conversion of the substrate to n-butanol, wherein expression of the enzymes encoded by the recombinant polynucleotides results in an increase in production of n-butanol as compared to a corresponding bacterium (e.g., same genus and species) lacking the recombinant polynucleotides, when cultured under the same conditions. In some embodiments, the methods further include substantially purifying the n-butanol. In some embodiments that may be combined with any of the preceding embodiments, the substrate comprises ethylene. In some embodiments that may be combined with any of the preceding embodiments, the substrate comprises glucose. In some embodiments that may be combined with any of the preceding embodiments, the substrate comprises ethanol.

BRIEF DESCRIPTION OF THE DRAWINGS

FIG. 4A shows a graph of cell density for n-butanol-producing strain grown in media with no carbon source (triangle with solid line), ethanol (circle with dashed line), or glucose (square dotted and dashed line). "Time" indicates time since adding M9 media. FIG. 4B shows n-butanol concentration produced by the n-butanol-producing strain after 3 days.

FIG. 5A shows the growth rate of strains in media containing glucose as the carbon source. FIG. 5B shows the growth rate of strains in media containing ethanol as the carbon source. "Time" indicates time since adding M9 media with glucose or ethanol, respectively.

DETAILED DESCRIPTION

Figure 1:
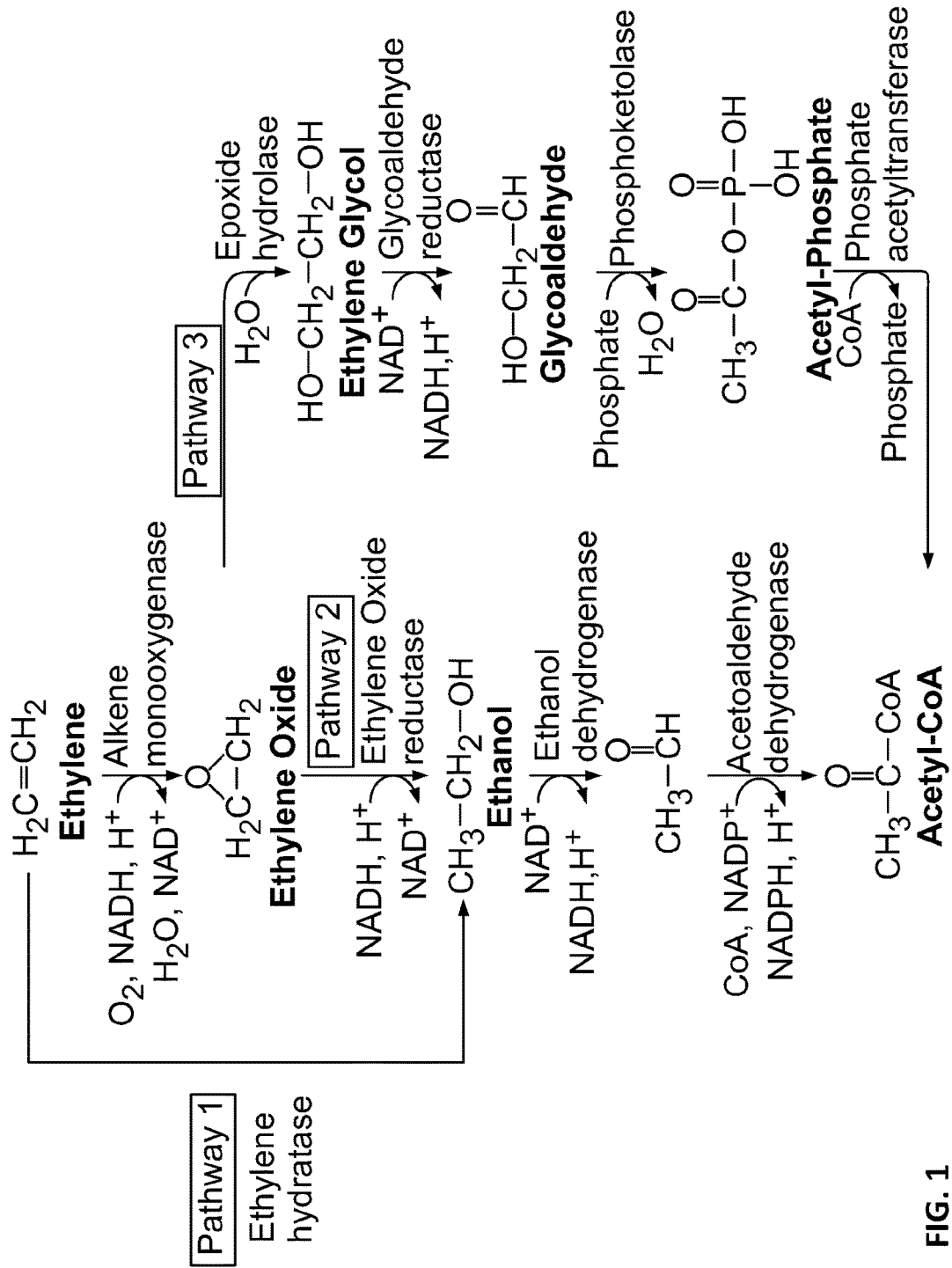
FIG. 1 illustrates three pathways for the enzymatic production of acetyl-CoA from ethylene.

The present disclosure provides recombinant bacteria with elevated production of ethanol and/or n-butanol from ethylene. Methods for the production of the recombinant bacteria, as well as for use thereof for production of ethanol and/or n-butanol are also provided.

In particular, the present disclosure provides efficient approaches for producing ethanol and n-butanol using recombinant bacteria. Advantageously, the recombinant bacteria and methods of use described herein allow the utilization of ethylene to generate higher value chemicals and liquid fuels. The use of these recombinant bacteria allows the generation of these valuable chemicals in a more cost-effective manner than existing methods.

Bacteria Engineered for Ethanol and/or n-Butanol Production

The present disclosure provides recombinant bacteria for use in the production of ethanol and/or n-butanol. The bacteria contain a recombinant polynucleotide encoding an ethylene hydratase (EH) or a recombinant polynucleotide encoding an alkene monooxygenase (AMO) and an ethylene oxide reductase (EOR). Expression of the EH, or the AMO and the EOR, results in an increase in production of ethanol as compared to corresponding bacteria lacking the polynucleotide (e.g., same genus and species) when cultured under the same conditions. Some bacteria contain a further recombinant polynucleotide encoding an alcohol/aldehyde dehydrogenase (AADH). Expression of either the EH, or the AMO and the EOR, in combination with the AADH results in an increase in production of acetyl-CoA as compared to corresponding bacteria lacking the recombinant polynucleotides (e.g., same genus and species) when cultured under the same conditions. Some bacteria contain a still further recombinant polynucleotide encoding an acetoaldehyde dehydrogenase (ALDH). Expression of either the EH, or the AMO and the EOR, in combination with the EDH and the ALDH results in an increase in production of acetyl-CoA as compared to corresponding bacteria lacking the recombinant polynucleotides (e.g., same genus and species) when cultured under the same conditions. The present disclosure also provides recombinant bacteria containing a recombinant polynucleotide encoding an alkene monooxygenase (AMO) and an epoxide hydrolase (EPH). Expression of the AMO and the EPH results in an increase in production of ethylene glycol as compared to corresponding bacteria lacking the polynucleotide (e.g., same genus and species) when cultured under the same conditions. Some bacteria contain a further recombinant polynucleotide encoding a glycoaldehyde reductase (GR). Expression of the AMO, the EPH, and the GR results in an increase in production of glycoaldehyde as compared to corresponding bacteria lacking the polynucleotide (e.g., same genus and species) when cultured under the same conditions. Some bacteria contain a still further recombinant polynucleotide encoding a phosphoketolase (PK). Expression of the AMO, the EPH, the GR, and the PK results in an increase in production of acetyl-phosphate as compared to corresponding bacteria lacking the polynucleotide (e.g., same genus and species) when cultured under the same conditions. Some bacteria contain a yet still further recombinant polynucleotide encoding a phosphate acetyltransferase (PA). Expression of the AMO, the EPH, the GR, the PK, and the PA results in an increase in production of acetyl-CoA as compared to corresponding bacteria lacking the polynucleotide (e.g., same genus and species) when cultured under the same conditions. In some embodiments, any of the above bacteria containing enzyme(s) whose expression results in an increase in production of acetyl-CoA may optionally contain recombinant polynucleotides encoding an acetoacetyl-CoA thiolase (AT), a 3-hydroxybutyryl-CoA dehydrogenase (HBD), a crotonase (CRT), a trans-enoyl-CoA reductase (TER), and an alcohol/aldehyde dehydrogenase (AADH). Expression of the AT, the HBD, the CRT, the TER, and the AADH, in combination with the enzyme(s) whose expression results in an increase in production of acetyl-CoA, results in an increase in production of n-butanol as compared to corresponding bacteria lacking the polynucleotide (e.g., same genus and species) when cultured under the same conditions.

As detailed above, described herein are bacteria containing two enzymatic pathways for increased production of ethanol: the ethylene hydratase (EH) pathway, and a pathway including both an alkene monooxygenase (AMO) and an ethylene oxide reductase (EOR). Further described herein are pathways for production of acetyl-CoA which, when combined with the expression of an acetoacetyl-CoA thiolase (AT), a 3-hydroxybutyryl-CoA dehydrogenase (HBD), a crotonase (CRT), a trans-enoyl-CoA reductase (TER), and an alcohol/aldehyde dehydrogenase (AADH), result in the increased production of n-butanol. These pathways are (1) EH and AADH; (2) EH, EDH, and ALDH; (3) AMO, EOR, and AADH; (4) AMO, EOR, EDH, and ALDH; and (5) AMO, EPH, GR, PK, and PA.

It is understood that the present disclosure describes the above pathways as separate only for the purpose of demonstrating that each is sufficient to carry out a desired enzymatic pathway. Any enzyme or combination of enzymes from one of the above pathways may be combined with any or all of the components of any of the enzymes from the other pathways. Stated another way, the pathways delineated above are not strictly limited to separate embodiments, but may be combined in any combination to achieve a desired biochemical pathway or production of a desired chemical or combination of desired chemicals, e.g., ethanol and/or n-butanol.

Enzymes

Table I provides the enzymes that have been inserted in various recombinant bacteria of the present disclosure.

TABLE I

Inserted Enzymes

| Inserted Enzyme (gene name if available) | Source | EcoGene No. | Enzyme NCBI No. |
|---|---|---|---|
| Oleate hydratase | Lysinibacillus fusiformis | — | ZP_07049769 |
| 2-haloacrylate hydratase | Pseudomonas sp. YL | — | BAJ13488 |
| Kievitone hydratase | Fusarium solani | — | AAA87627.1 |
| Toluene monooxygenase (T4MO) | Pseudomonas mendocina | — | M65106.1 |
| Toluene monooxygenase (TOM) | Burkholderia cepacia | — | AF349675 |
| Alcohol/aldehyde dehydrogenase (AdhE) | E. coli | EG10031 | NP_41575.1 |
| Ethanol dehydrogenase (AdhP) | E. coli | EG12622 | NP_415995.4 |
| Acetoaldehyde dehydrogenase (MhpF) | E. coli | EG13625 | NP_414885.1 |
| Acetoaldehyde dehydrogenase (EdgE) | Listeria monocytogenes | — | NP_464704.1 |
| Acetoacetyl-CoA thiolase (AtoB) | E. coli | EG11672 | NP_416728.1 |
| 3-hydroxybutyryl-CoA dehydrogenase (Hbd) | Clostridium acetobutylicum | — | AAA95971 |
| Crotonase (Crt) | Clostridium acetobutylicum | — | WP_010965999.1 |
| Trans-enoyl-CoA reductase (Ter) | Treponema denticola | — | NP_971211.1 |
| Alcohol/aldehyde dehydrogenase (AdhE2) | Clostridium acetobutylicum | — | AF321779_1 |

Several classification schemes exist to enable one of skill to identify homologous genes, or proteins with homologous functions or enzymatic properties, across various bacterial species. Enzymatic reactions can be classified according to their Enzyme Commission (EC) number. The EC number associated with a given enzyme specifies the classification of the type of enzymatic reaction that a given enzyme is capable of catalyzing. EC numbers do not specify identities of enzymes, but instead specify the identity of the chemical reaction that a given enzyme catalyzes. Similarly, proteins can also be assigned Gene Ontology (GO) terms. GO terms attempt to further define the given role and/or function of a protein in a living organism by specifying protein function in terms of a cellular component, a biological process, and/or a molecular function. For example, two enzymes from two different species of organisms that catalyze the same chemical reaction could be assigned the same EC classification and GO term annotation, despite that the respective enzymes are endogenous to different organisms. EC and GO term classifications are helpful to those skilled in the art in identifying the molecular function and/or activity of a given protein outside of knowing its unique identifying classification with regard to the organism it came from, such as its NCBI (National Council for Biotechnology) identifier. EC and GO term classifications may encompass broad or very narrow enzymatic activities and functions, and many proteins are classified under several often overlapping EC and GO terms. The classifications listed in this disclosure are included to describe enzymes and genes that could be utilized in certain embodiments. They are provided to help those skilled in the art understand the enzymatic activity or class of interest and are not meant to limit or restrict choice of enzymes in the embodiments.

Enzymes for Ethanol Production

Certain aspects of the present disclosure relate to bacteria expressing enzymes enabling the conversion of ethylene to ethanol for the production of ethanol, as well as their methods of use. Ethylene hydratase (EH) activity converts ethylene (the term "ethene" may be used interchangeably herein) to ethanol. While bacteria containing an EH enzyme have been identified, the reaction catalyzing the conversion of ethylene to ethanol has not been identified in nature. Any enzyme catalyzing the formation of ethanol from ethylene may be termed an ethylene hydratase of the present disclosure.

In some embodiments, an enzyme characterized to have hydratase activity against a substrate related to ethylene may be used as an EH of the present disclosure. In some embodiments, the EH is an alkene hydratase. In some embodiments, the EH is an oleate hydratase. Oleate hydratase may refer to any enzyme catalyzing the conversion of oleate and water to (R)-10-hydroxystearate. This enzymatic reaction belongs to the classification EC 4.2.1.53. Oleate hydratases share the molecular function of GO term ID GO:0050151. Any protein characterized with these EC classifications and/or GO terms may possess catalytic oleate hydratase activity. More descriptions of oleate hydratases may be found in O'Connell et al., Bioengineered 4, 313-321, 2013; Joo et al., Biochimie 94, 907-915, 2012; Kim et al., Appl Microbiol Biotechnol 95, 929-937, 2012; Bevers et al., J Bacteriol 191, 5010-5012, 2009; and Kisic et al., Lipids 6, 541-545, 1971. In some embodiments, the oleate hydratase is a Lysinibacillus fusiformis oleate hydratase (see Table I for sequence reference).

In some embodiments, the EH is a 2-haloacrylate hydratase. 2-haloacrylate hydratase may refer to any enzyme catalyzing the conversion of 2-chloroacrylate to pyruvate using $FADH_2$ as a co-factor. More description of 2-haloacrylate hydratases may be found in Mowafy et al., Appl Environ Microbiol 76, 6032-6037, 2010. In some embodiments, the 2-haloacrylate hydratase is a Pseudomonas species 2-haloacrylate hydratase (see Table I for sequence reference). In some embodiments, the 2-haloacrylate hydratase is a Pseudomonas species strain YL 2-haloacrylate hydratase.

In some embodiments, the EH is a kievitone hydratase. Kievitone hydratase may refer to any enzyme catalyzing the conversion of kievitone and water to kievitone hydrate. This enzymatic reaction belongs to the classification EC 4.2.1.95. Kievitone hydratases share the molecular function of GO term ID GO:0050015. Any protein characterized with these EC classifications and/or GO terms may possess catalytic kievitone hydratase activity. More descriptions of kievitone hydratases may be found in Li et al., *Mol Plant Microbe Interact* 8, 388-397, 1995; Turbek et al., *Phytochemistry* 29, 2841-2846, 1990; Turbek et al., *FEMS Microbiol Lett* 73, 187-190, 1992. In some embodiments, the kievitone hydratase is a *Fusarium solani* kievitone hydratase (see Table I for sequence reference).

Ethylene may also be converted into ethanol using the enzymatic activities of alkene monooxygenase (AMO) and ethylene oxide reductase (EOR). Alkene monooxygenase may refer to any enzyme catalyzing the conversion of ethylene to ethylene oxide (the term "oxirane" may be used interchangeably herein). In some embodiments, an AMO may catalyze the conversion of propene to 1,2-epoxypropane using NADH and oxygen. This enzymatic reaction belongs to the classification EC 1.14.13.69. In some embodiments, an AMO may catalyze the production of oxirane (also known as ethylene oxide) from ethylene. Alkene monooxygenases share the molecular function of GO term ID GO:0018645. Any protein characterized with these EC classifications and/or GO terms may possess catalytic alkene monooxygenase activity. More descriptions of alkene monooxygenases may be found in Ginkel et al., *Appl Microbiol Biotechnol* 24, 334-337 (1986); Coleman and Spain, *J Bacteriol* 185, 5536-5545 (2003); Mattes et al., *Arch Microbiol* 183, 95-106 (2005); Perry and Smith, *J Biomol Screen* 11, 553-556 (2006).

In some embodiments, an enzyme characterized to have alkene monooxygenase activity against a substrate related to ethylene may be used as an AMO of the present disclosure. In some embodiments, the AMO is a toluene monooxygenase. In some embodiments, the toluene monooxygenase hydratase is a *Pseudomonas mendocina* toluene monooxygenase (see Table I for sequence reference). In some embodiments, the toluene monooxygenase hydratase is a *Burkholderia cepacia* toluene monooxygenase (see Table I for sequence reference). More descriptions of toluene monooxygenases may be found in McClay et al., *Appl Environ Microbiol* 66, 1877-1882, 2000. In some embodiments, the AMO is a styrene monooxygenase.

Ethylene oxide reductase (EOR) may refer to any enzyme catalyzing the conversion of ethylene oxide to ethanol using NADH. No NADH dependent epoxide reductase is known in the art. In some embodiments, the EOR is a $NAD^+$ dependent formate dehydrogenase. Without wishing to be bound to theory, it is thought that this enzyme may catalyze the reaction since its active site is similar in size to ethylene oxide. $NAD^+$ dependent formate dehydrogenase may refer to any enzyme catalyzing the conversion of formate to carbon dioxide using NAD+ as a co-factor. This enzymatic reaction belongs to the classification EC 1.2.1.2. $NAD^+$ dependent formate dehydrogenases share the molecular function of GO term ID GO:0008863. Any protein characterized with these EC classifications and/or GO terms may possess catalytic $NAD^+$ dependent formate dehydrogenase activity. More descriptions of $NAD^+$ dependent formate dehydrogenases may be found in Ferry, *FEMS Microbiol Rev* 7, 377-382, 1990. In some embodiments, the $NAD^+$ dependent formate dehydrogenase is a *Candida methylica* $NAD^+$ dependent formate dehydrogenase (see, e.g., NCBI CAA57036.1). In some embodiments, the $NAD^+$ dependent formate dehydrogenase is a *Burkholderia stabilis* $NAD^+$ dependent formate dehydrogenase (see, e.g., NCBI ACF35003.1). In some embodiments, the $NAD^+$ dependent formate dehydrogenase is a *Pseudomonas* sp. strain 101 $NAD^+$ dependent formate dehydrogenase (see, e.g., Uniprot P33160).

Enzymes for n-Butanol Production

Certain aspects of the present disclosure relate to bacteria expressing enzymes enabling the conversion of ethylene to n-butanol for the production of n-butanol, as well as their methods of use. In some embodiments, bacteria expressing enzymes enabling the production of ethanol (e.g., EH, or AMO and EOR) may further express enzymes enabling the conversion of this ethanol to acetyl-CoA.

Ethanol may be converted to acetyl-CoA using the enzymatic activity of an alcohol/aldehyde dehydrogenase (AADH). Alcohol/aldehyde dehydrogenase (AADH) may refer to any enzyme catalyzing the conversion of an alcohol to an aldehyde or ketone using NAD+ as a co-factor and the conversion of acetaldehyde to acetyl-CoA using NAD+ and CoA as co-factors. These enzymatic reactions belong to the classifications EC 1.1.1.1 and EC 1.2.1.10. Alcohol/aldehyde dehydrogenases share the molecular function of GO term IDs GO:0004022 and GO:0008774. Any protein characterized with these EC classifications and/or GO terms may possess catalytic alcohol/aldehyde dehydrogenase activity. In some embodiments, the alcohol/aldehyde dehydrogenase is an *E. coli* AdhE (see Table I for sequence reference). In some embodiments, the AADH catalyzes the conversion of butylaldehyde to n-butanol. In some embodiments, the alcohol/aldehyde dehydrogenase is a *Clostridium acetobutylicum* AdhE2.

Ethanol may also be converted to acetyl-CoA using the enzymatic activities of an ethanol dehydrogenase (EDH) and an acetoaldehyde dehydrogenase (ALDH). Ethanol dehydrogenase (EDH) may refer to any enzyme catalyzing the conversion of an alcohol to an aldehyde or ketone using NAD+ as a co-factor. This enzymatic reaction belongs to the classification EC 1.1.1.1. Ethanol dehydrogenases share the molecular function of GO term ID GO:0004022. Any protein characterized with these EC classifications and/or GO terms may possess catalytic ethanol dehydrogenase activity. In some embodiments, the ethanol dehydrogenase is an *E. coli* AdhP. Acetoaldehyde dehydrogenase (ALDH) may refer to any enzyme catalyzing the conversion of acetaldehyde to acetyl-CoA using NAD+ and CoA as co-factors. This enzymatic reaction belongs to the classification EC 1.2.1.10. Acetoaldehyde dehydrogenases share the molecular function of GO term ID GO: 0008774. Any protein characterized with these EC classifications and/or GO terms may possess catalytic acetoaldehyde dehydrogenase activity. In some embodiments, the acetoaldehyde dehydrogenase is an *E. coli* MhpF. In some embodiments, the acetoaldehyde dehydrogenase is a *Listeria monocytogenes* EdgE. In a preferred embodiment using the combination of ethanol dehydrogenase and acetoaldehyde dehydrogenase, the bacteria express an *E. coli* AdhP and a *Listeria monocytogenes* EdgE.

Ethylene may be converted to acetyl-CoA using the enzymatic activities of an alkene monooxygenase (AMO), an epoxide hydrolase (EPH), a glycoaldehyde reductase (GR), a phosphoketolase (PK), and a phosphate acetyltransferase (PA). Epoxide hydrolase may refer to any enzyme catalyzing the conversion of an epoxide to glycol. This enzymatic reaction belongs to the classification EC 3.3.2.10. Epoxide hydrolase share the molecular function of GO term ID GO:0004301. Any protein characterized with these EC classifications and/or GO terms may possess catalytic epoxide hydrolase activity. Glycoaldehyde reductase may refer to any enzyme catalyzing the conversion of ethylene glycol to glycoaldehyde. The general aldehyde reductase enzymatic reaction belongs to the classification EC 1.1.1.21. Aldehyde reductases share the molecular function of GO term ID GO:0004032. Any protein characterized with these EC classifications and/or GO terms that acts on ethylene glycol may possess catalytic glycoaldehyde reductase activity. Phosphoketolase may refer to any enzyme catalyzing the conversion of glycoaldehyde to acetyl-phosphate. This enzymatic reaction belongs to the classification EC 4.1.2.9. Phosphoketolases share the molecular function of GO term ID GO:0050193. Any protein characterized with these EC classifications and/or GO terms may possess catalytic phosphoketolase activity. Phosphate acetyltransferase may refer to any enzyme catalyzing the conversion of acetyl-phosphate to acetyl-CoA. This enzymatic reaction belongs to the classification EC 2.3.1.8. Phosphate acetyltransferases share the molecular function of GO term ID GO:0008959. Any protein characterized with these EC classifications and/or GO terms may possess catalytic phosphate acetyltransferase activity.

Certain aspects of the present disclosure relate to bacteria expressing enzymes enabling the conversion of acetyl-CoA to n-butanol for the production of n-butanol, as well as their methods of use. More descriptions of the synthetic n-butanol pathway are provided in Atsumi et al., *Metab Eng* 10, 305-311, 2008 and Shen et al., *Appl. Environ. Microbiol.* 77, 2905-2915, 2011. In some embodiments, bacteria expressing enzymes enabling the increased production of acetyl-CoA also express yet still further recombinant polynucleotides encoding an acetoacetyl-CoA thiolase (AT), a 3-hydroxybutyryl-CoA dehydrogenase (HBD), a crotonase (CRT), a trans-enoyl-CoA reductase (TER), and an alcohol/aldehyde dehydrogenase (AADH). Acetoacetyl-CoA thiolase (also known as acetoacetyl-CoA thiolase) may refer to any enzyme catalyzing the conversion of acetyl-CoA to acetoacetyl-CoA. This enzymatic reaction belongs to the classification EC 2.3.1.9. Acetoacetyl-CoA thiolases share the molecular function of GO term ID GO:0003985. Any protein characterized with these EC classifications and/or GO terms may possess catalytic acetoacetyl-CoA thiolase activity. In some embodiments, the acetoacetyl-CoA thiolase is an *E. coli* AtoB. 3-hydroxybutyryl-CoA dehydrogenase may refer to any enzyme catalyzing the conversion of acetoacetyl-CoA to 3-hydroxybutyryl-CoA. This enzymatic reaction belongs to the classification EC 1.1.1.157. 3-hydroxybutyryl-CoA dehydrogenases share the molecular function of GO term ID GO:0008691. Any protein characterized with these EC classifications and/or GO terms may possess catalytic 3-hydroxybutyryl-CoA dehydrogenase. In some embodiments, the 3-hydroxybutyryl-CoA dehydrogenase is a *C. acetobutylicum* Hbd. Crotonase (also known as enoyl-CoA hydratase) may refer to any enzyme catalyzing the conversion of 3-hydroxybutyryl-CoA to crotonyl-CoA. This enzymatic reaction belongs to the classification EC 4.2.1.17. Crotonases share the molecular function of GO term ID GO:0004300. Any protein characterized with these EC classifications and/or GO terms may possess catalytic crotonase activity. In some embodiments, the crotonase is a *C. acetobutylicum* Crt. Trans-enoyl-CoA reductase may refer to any enzyme catalyzing the conversion of crotonyl-CoA to butyryl-CoA. This enzymatic reaction belongs to the classification EC 1.3.1.38. Trans-enoyl-CoA reductases share the molecular function of GO term ID GO:0019166.

Any protein characterized with these EC classifications and/or GO terms may possess catalytic trans-enoyl-CoA reductase activity. In some embodiments, the trans-enoyl-CoA reductase is a *T. denticola* Ter. The final step in this pathway for n-butanol production may be catalyzed by an AADH as described above.

Bacterial Cells

The present disclosure provides recombinant bacteria. Any culturable bacteria are suitable for use in the compositions and methods described herein. The term "bacteria" refers to a domain of prokaryotic organisms. Bacteria include at least 11 distinct groups as follows: (1) Gram-positive (gram+) bacteria, of which there are two major subdivisions: (1) high G+C group (Actinomycetes, Mycobacteria, *Micrococcus*, others) (2) low G+C group (*Bacillus, Clostridia, Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles*.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

Although *E. coli* was utilized in exemplary embodiments, the present disclosure is not limited to this genus and species of bacteria. It is understood that many bacterial species can be modified to produce ethanol and/or n-butanol. It is further understood that various microorganisms can act as "sources" for genetic material encoding target enzymes (e.g., ethylene hydratases, alkene monooxygenases, ethylene oxide reductases, alcohol/aldehyde dehydrogenases, ethanol dehydrogenases, acetaldehyde dehydrogenases, epoxide hydrolases, glycoaldehyde reductases, phosphoketolases, acetyltransferases, acetoacetyl-CoA thiolases, 3-hydroxybutyryl-CoA dehydrogenases, crotonases, and trans-enoyl-CoA reductases) suitable for use in recombinant bacteria provided herein.

Exemplary embodiments use *E. coli* as the host bacterial species because of the extensive expertise and reagents available for this common model bacterium. However, protocols and reagents for recombinantly expressing proteins in a wide variety of bacterial host species are known in the art (Current Protocols in Microbiology. Hoboken: Wiley, 2013; Neidhardt, F. C. *Escherichia coli* and *Salmonella*: Cellular and Molecular Biology. $2^{nd}$ ed. Washington, D.C.: ASM Press, 1996). Furthermore, because of the physiological similarities between bacterial species, existing protocols and reagents for recombinantly expressing a polypeptide in one species (e.g., *E. coli*) may readily function without undue experimentation in another species.

Methods of Producing and Purifying Ethanol and n-Butanol

The present disclosure provides methods of producing ethanol or n-butanol. These methods involve providing recombinant bacteria with one or more recombinant polynucleotides and culturing the recombinant bacteria in a culture medium with a substrate under conditions that enable the bacteria to convert the substrate into ethanol or n-butanol, thereby producing ethanol or n-butanol in higher amounts or at a higher rate than bacteria of the same species lacking the recombinant polynucleotides. The methods of the present disclosure may be used to produce ethanol and n-butanol separately or in combination.

In some embodiments, the methods for producing methods of producing ethanol or n-butanol include a culture medium for culturing the recombinant bacteria. "Culture medium" as used herein refers to any composition or broth that supports the growth of the bacteria of the present disclosure. Suitable culture media may be liquid or solid and contain any nutrients, salts, buffers, elements, and other compounds that support the growth and viability of cells. Common nutrients of a culture medium may include sources of nitrogen, carbon, amino acids, carbohydrates, trace elements, vitamins, and minerals. These nutrients may be added as individual components (as in a defined culture medium) or as constituents of a complex extract (for example, yeast extract). A culture medium may be nutrient-rich to support rapid growth or minimal to support slower growth. A culture medium may also contain any agent used to inhibit the growth of or kill contaminating organisms (e.g., an antibiotic). A culture medium may also contain any compound used to control the activity of an inducible promoter or enzyme (as one example, IPTG may be included to induce expression of any polynucleotides controlled by a lac operon or functionally similar promoter). Many examples of suitable culture media are well known in the art and include without limitation M9 medium, Lysogeny Broth (LB), Terrific Broth (TB), and YT broth.

In some embodiments, recombinant bacteria are cultured. Culturing bacteria refers to providing the bacteria with a suitable nutrient source (such as a culture medium of the present disclosure) under conditions that allow for bacterial growth. These conditions may include pH, temperature, gas levels (e.g., oxygen and carbon dioxide), pressure, light, and cell density. Suitable ranges for each of these parameters may differ depending upon the particular bacteria, desired metabolic state of the bacteria, or the activity of any enzymes expressed by the bacteria. Culturing conditions and methods suitable for a wide range of bacterial species are well known in the art.

In some embodiments, the culture medium contains a substrate that is converted by the recombinant bacteria to ethanol or n-butanol. Suitable substrates may include any carbon source used by bacteria to produce acetyl-CoA, isobutyryl-CoA, pyruvate, an aldehyde, an ester, or an alcohol. In some embodiments, the substrate comprises ethylene. Ethylene may be added to a suitable nutrient source (such as a culture medium of the present disclosure) in any state. In some embodiments, ethylene is added as a percentage of the gases present in the atmosphere in which the bacteria are cultured at a concentration sufficient for n-butanol production (for example, without limitation, at 1.5%).

In some embodiments, the substrate comprises glucose, e.g., the substrate may be a reduced carbon source that is metabolized by the bacteria via glycolysis into pyruvate or acetyl-CoA (e.g., glucose, glycerol, sugars, starches, and lignocellulosics, including glucose derived from cellulose and $C_5$ sugars derived from hemicellulose, such as xylose). In some embodiments, the substrate may be ethanol, used in the bacterial production of n-butanol. In some embodiments, the substrate may be an amino acid (e.g., valine or isoleucine) or a compound involved in an amino acid biosynthesis pathway. A substrate may be a constituent of the culture medium, or it may be exogenously supplemented to the culture medium. A substrate may be continuously present in the culture medium, or it may be supplemented during bacterial growth. A substrate may be present in any desired amount in the culture medium, depending upon the metabolic activity and/or output of the bacteria or their tolerance of the substrate.

In some embodiments, the bacteria are used to produce ethanol. In some embodiments, the bacteria contain polynucleotides encoding an alkene monooxygenase (AMO) and an ethylene oxide reductase (EOR). The genes encoding the AMO and the EOR components may be part of the same polynucleotide, or separate polynucleotides. They may be regulated by shared or distinct regulatory elements, such as promoters. In some embodiments, the AMO and EOR genes may be controlled by an inducible promoter (e.g., the lac operon or a functionally similar element). In some embodiments, bacteria may be grown in the absence of AMO and EOR expression, then induced to express the AMO and EOR at the same time a suitable substrate for ethanol production is added to the culture medium. Alternatively, the AMO and EOR may be expressed constitutively. Any other combination of enzymes described herein may be expressed from the same polynucleotide, or separate polynucleotides, and regulated in an inducible or constitutive manner.

In some embodiments, the methods of the present disclosure may include a step of substantially purifying the ethanol or n-butanol produced by the recombinant bacteria. In some embodiments, ethanol or n-butanol is evaporated using any gas stripping method known in the art, for example by using a Graham condenser. Suitable gas stripping methods need not include a heating step. In other embodiments, ethanol or n-butanol may be distilled from the culture medium. Ethanol or n-butanol may also be extracted from the culture medium using a solvent and distilled from the extract. In some embodiments, ethanol or n-butanol is purified by any liquid-liquid extraction technique known in the art. In some embodiments, ethanol or n-butanol is purified by any pervaporation technique known in the art. Various methods for purifying ethanol or n-butanol from a microbial culture are known in the art (see, e.g., Shen et al., *Appl Environ Microbiol,* 77, 2905-2915, 2011).

Ethanol or n-butanol may be purified at any step in the culturing process. Many methods for product generation and purification from bacterial cultures are known in the art (see, e.g., Villadsen et al., Bioreaction Engineering Principles. $3^{rd}$ ed. Springer; 2011). Ethanol or n-butanol purification may be performed continuously during culturing, as in a continuous culture method, or it may be performed separately from or after culturing, as in a batch or fed-batch culture method.

Supplemental Information

The practice of the present disclosure will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989); Oligonucleotide Synthesis (Gait, ed., 1984); Animal Cell Culture (Freshney, ed., 1987); Handbook of Experimental Immunology (Weir & Blackwell, eds.); Gene Transfer Vectors for Mammalian Cells (Miller & Calos, eds., 1987); Current Protocols in Molecular Biology (Ausubel et al., eds., 1987); PCR: The Polymerase Chain Reaction, (Mullis et al., eds., 1994); Current Protocols in Immunology (Coligan et al., eds., 1991); The Immunoassay Handbook (Wild ed., Stockton Press NY, 1994); Bioconjugate Techniques (Hermanson, ed., Academic Press, 1996); and Methods of Immunological Analysis (Masseyeff, Albert, and Staines, eds., Weinheim: VCH Verlags gesellschaft mbH, 1993).

The present disclosure identifies specific polynucleotides/ genes useful in the methods, compositions and organisms of the disclosure. However, it should be recognized that absolute identity to such genes is not necessary, as substantially similar polynucleotides/genes that perform substantially similar functions can also be used in the compositions and methods of the present disclosure. For example, changes in a particular gene or polynucleotide containing a sequence encoding a polypeptide or enzyme can be made and screened for expression and/or activity. Typically such changes include conservative and/or silent mutations.

Due to the inherent degeneracy of the genetic code, polynucleotides which encode substantially the same or functionally equivalent polypeptides can also be used to clone and express the same polypeptides (e.g., enzymes). As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of *E. coli*, a process sometimes called "codon optimization" (see, e.g., Murray et al., *Nucl Acids Res*, 17:477-508, 1989).

Those of skill in the art will recognize that, due to the degenerate nature of the genetic code, a variety of DNA compounds differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as they modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for generating metabolites are encompassed by the microorganisms and methods provided herein. The term "homologs" used with respect to an original enzyme or gene of a first family or species refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Homologs can be identified by reference to various databases and identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. Thus, the term "homologous proteins" is defined to mean that the two proteins have similar amino acid sequences.

As used herein, two proteins (or a region of the proteins) are substantially homologous when the amino acid sequences have at least about 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 50%, typically at least 75%, and even more typically at least 80%, 85%, 90%, 95% or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity. For blastn, the default parameters are Gap opening penalty=5 and Gap extension penalty=2. For blastp, the default parameters are Gap opening penalty=11 and Gap extension penalty=1.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted using known algorithms (e.g., by the local homology algorithm of Smith and Waterman, *Adv Appl Math*, 2:482, 1981; by the homology alignment algorithm of Needleman and Wunsch, *J Mol Biol*, 48:443, 1970; by the search for similarity method of Pearson and Lipman, *Proc Natl Acad Sci USA*, 85:2444, 1988; by computerized implementations of these algorithms FASTDB (Intelligenetics), BLAST (National Center for Biomedical Information), GAP, BESTFIT, FASTA, and TFASTA in the Wisconsin Genetics Software Package (Genetics Computer Group, Madison, Wis.), or by manual alignment and visual inspection.

A preferred example of an algorithm that is suitable for determining percent sequence identity and sequence similarity is the FASTA algorithm (Pearson and Lipman, *Proc Natl Acad Sci USA*, 85:2444, 1988; and Pearson, *Methods Enzymol*, 266:227-258, 1996). Preferred parameters used in a FASTA alignment of DNA sequences to calculate percent identity are optimized, BL50 Matrix 15:−5, k-tuple=2; joining penalty=40, optimization=28; gap penalty-12, gap length penalty=−2; and width=16.

Another preferred example of algorithms suitable for determining percent sequence identity and sequence similarity are the BLAST and BLAST 2.0 algorithms (Altschul et al., *Nuc Acids Res*, 25:3389-3402, 1977; and Altschul et al., *J Mol Biol*, 215:403-410, 1990, respectively). BLAST and BLAST 2.0 are used, with the parameters described herein, to determine percent sequence identity for the nucleic acids and proteins of the disclosure. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (Henikoff and Henikoff, *Proc Natl Acad Sci USA*, 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc Natl Acad Sci USA*, 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method (Feng and Doolittle, *J Mol Evol*, 35:351-360, 1987), employing a method similar to a published method (Higgins and Sharp, *CABIOS* 5:151-153, 1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc Acids Res*, 12:387-395, 1984).

Another preferred example of an algorithm that is suitable for multiple DNA and amino acid sequence alignments is the CLUSTALW program (Thompson et al., *Nucl Acids. Res*, 22:4673-4680, 1994). ClustalW performs multiple pairwise comparisons between groups of sequences and assembles them into a multiple alignment based on homology. Gap open and Gap extension penalties were 10 and 0.05 respectively. For amino acid alignments, the BLOSUM algorithm can be used as a protein weight matrix (Henikoff and Henikoff, *Proc Natl Acad Sci USA*, 89:10915-10919, 1992).

Polynucleotides of the disclosure further include polynucleotides that encode conservatively modified variants of the polypeptides of Table I. "Conservatively modified variants" as used herein include individual mutations that result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure. The following eight groups contain amino acids that are conservative substitutions for one another: 1. Alanine (A), Glycine (G); 2. Aspartic acid (D), Glutamic acid (E); 3. Asparagine (N), Glutamine (Q); 4. Arginine (R), Lysine (K); 5. Isoleucine (I), Leucine (L), Methionine (M), Valine (V); 6. Phenylalanine (F), Tyrosine (Y), Tryptophan (W); 7. Serine (S), Threonine (T); and 8. Cysteine (C), Methionine (M).

The terms "derived from" or "of" when used in reference to a nucleic acid or protein indicates that its sequence is identical or substantially identical to that of an organism of interest. For instance, "an oleate hydratase derived from

*Lysinibacillus fusiformis*," "an oleate hydratase of *Lysinibacillus fusiformis*," or "a *Lysinibacillus fusiformis* oleate hydratase" refers to an oleate hydratase enzyme having a sequence identical or substantially identical to a native oleate hydratase enzyme of *Lysinibacillus fusiformis*. The terms "derived from" and "of" when used in reference to a nucleic acid or protein do not indicate that the nucleic acid or protein in question was necessarily directly purified, isolated or otherwise obtained from an organism of interest. Thus by way of example, an isolated nucleic acid containing an oleate hydratase coding region of *Lysinibacillus fusiformis* need not be obtained directly from this species, instead the isolated nucleic acid may be prepared synthetically using methods known to one of skill in the art.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction. As used herein, the term "transformed" refers to a cell that has an exogenous polynucleotide sequence integrated into its genome or as an episomal plasmid that is maintained for at least two generations.

The terms "coding region," "open reading frame" and "ORF" refers to a sequence of codons extending from an initiator codon (ATG) to a terminator codon (TAG, TAA or TGA), which can be translated into a polypeptide.

In some embodiments of the disclosure, the coding sequences of the polynucleotides are operably linked to a promoter. In some embodiments, the promoter is an inducible promoter. In some embodiments, the promoter is a constitutive promoter. As used herein, "inducible promoter" refers to a promoter that drives expression of a polynucleotide to which it is operably linked upon cellular perception of a stimulus. Likewise, inducible promoters can terminate expression of a polynucleotide to which it is operably linked upon removal of a stimulus. An example of an inducible promoter in the present disclosure is the isopropyl-β-D-thiogalactoside (IPTG) inducible promoter, in which this promoter drives expression of a polynucleotide to which it is operably linked upon perception of IPTG, an exogenous chemical. Constitutive promoters are those promoters that are substantially insensitive to regulation by external stimuli and promote expression of a given polynucleotide in an essentially constant manner.

As used herein, "recombinant" or "heterologous" or "heterologous polynucleotide" or "recombinant polynucleotide" refers to a polynucleotide wherein the exact nucleotide sequence of the polynucleotide is foreign to (i.e., not naturally found in) a given host. These terms may also refer to a polynucleotide sequence that may be naturally found in a given host, but in an unnatural (e.g., greater than or less than expected) amount, or additionally if the sequence of a polynucleotide comprises two or more subsequences that are not found in the same relationship to each other in nature. For example, regarding the latter, a recombinant polynucleotide could have two or more sequences from unrelated polynucleotides or from homologous nucleotides arranged to make a new polynucleotide. Specifically, the present disclosure describes the introduction of a recombinant vector into a microorganism, wherein the vector contains a polynucleotide coding for a polypeptide that is not normally found in the microorganism or contains a foreign polynucleotide coding for a substantially homologous polypeptide that is normally found in the host organism. With reference to the host cell's genome, then, the polynucleotide sequence that encodes the polypeptide is recombinant or heterologous. "Recombinant" may also be used to refer to an organism that contains one or more heterologous polynucleotides.

As used herein, the term "vector" refers to a polynucleotide construct designed to introduce nucleic acids into one or more cell types. Vectors include cloning vectors, expression vectors, shuttle vectors, plasmids, cassettes and the like. As used herein, the term "plasmid" refers to a circular double-stranded DNA construct used as a cloning and/or expression vector. Some plasmids take the form of an extrachromosomal self-replicating genetic element (episomal plasmid) when introduced into a host cell.

In some embodiments, at least one of the recombinant polynucleotides is stably integrated into the genome of the bacterium. Some plasmids integrate into a host chromosome (integrative plasmid) when introduced into a host cell, and are thereby replicated along with the host cell genome. Moreover, certain vectors are capable of directing the expression of coding regions to which they are operatively linked. Such vectors are referred to herein as "expression vectors." Thus expression vectors cause cells to express polynucleotides and/or polypeptides other than those native to the cells, or in a manner not native to the cells).

Genetic modifications that result in an increase in gene expression or function can be referred to as amplification, overproduction, overexpression, activation, enhancement, addition, or up-regulation of a gene. More specifically, reference to increasing the action (or activity) of enzymes or other proteins discussed herein generally refers to any genetic modification of the host cell in question which results in increased expression and/or functionality (biological activity) of the enzymes or proteins and includes higher activity or action of the proteins (e.g., specific activity or in vivo enzymatic activity), reduced inhibition or degradation of the proteins, and overexpression of the proteins. For example, gene copy number can be increased, expression levels can be increased by use of a promoter that gives higher levels of expression than that of the native promoter, or a gene can be altered by genetic engineering or classical mutagenesis to increase the biological activity of an enzyme or action of a protein. Combinations of some of these modifications are also possible.

Genetic modifications which result in a decrease in gene expression, in the function of the gene, or in the function of the gene product (i.e., the protein encoded by the gene) can be referred to as inactivation (complete or partial), deletion, interruption, blockage, silencing, or down-regulation, or attenuation of expression of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity or action). The term "functional deletion" as used herein refers to a genetic modification of a gene that serves to substantially eliminate transcription, translation or activity of any resulting gene product. More specifically, reference to decreasing the action of proteins discussed herein generally refers to any genetic modification in the host cell in question, which results in decreased expression and/or functionality (biological activity) of the proteins and includes decreased activity of the proteins (e.g., decreased enzymatic activity), increased inhibition or degradation of the proteins as well as a reduction or elimination of expression of the proteins. Combinations of some of these modifications are also possible.

The terms "decrease," "reduce" and "reduction" as used in reference to biological function (e.g., enzymatic activity, production of compound, expression of a protein, etc.) refer to a measurable lessening in the function by preferably at least 10%, more preferably at least 50%, still more preferably at least 75%, and most preferably at least 90%. Depending upon the function, the reduction may be from 10% to 100%. The term "substantial reduction" and the like refers to a reduction of at least 50%, 75%, 90%, 95% or 100%.

The terms "increase," "elevate" and "elevation" as used in reference to biological function (e.g., enzymatic activity, production of compound, expression of a protein, etc.) refer to a measurable augmentation in the function by preferably at least 10%, more preferably at least 50%, still more preferably at least 75%, and most preferably at least 90%. Depending upon the function, the elevation may be from 10% to 100%; or at least 10-fold, 100-fold, or 1000-fold up to 100-fold, 1000-fold or 10,000-fold or more. The term "substantial elevation" and the like refers to an elevation of at least 50%, 75%, 90%, 95% or 100%.

The terms "isolated" and "purified" as used herein refers to a material that is removed from at least one component with which it is naturally associated (e.g., removed from its original environment). The term "isolated," when used in reference to a biosythetically-produced ester, refers to an ester that has been removed from the culture medium of the bacteria that produced the ester. As such an isolated ester is free of extraneous or unwanted compounds (e.g., substrate molecules, bacterial components, etc.).

As used herein, the singular form "a", "an", and "the" includes plural references unless indicated otherwise.

The phrase "comprising" as used herein is open-ended, indicating that such embodiments may include additional elements. In contrast, the phrase "consisting of" is closed, indicating that such embodiments do not include additional elements (except for trace impurities). The phrase "consisting essentially of" is partially closed, indicating that such embodiments may further comprise elements that do not materially change the basic characteristics of such embodiments. It is understood that aspects and embodiments described herein as "comprising" include "consisting" and/or "consisting essentially of" aspects and embodiments.

EXAMPLES

To better facilitate an understanding of embodiments of the disclosure, the following examples are presented. The following examples are merely illustrative and are not meant to limit any embodiments of the present disclosure in any way.

Abbreviations: ethylene hydratase (EH); alkene monooxygenase (AMO); ethylene oxide reductase (EOR); alcohol/aldehyde dehydrogenase (AADH); ethanol dehydrogenase (EDH); acetoaldehyde dehydrogenase (ALDH); epoxide hydrolase (EPH); glycoaldehyde reductase (GR); phosphoketolase (PK); phosphate acetyltransferase (PA); acetoacetyl-CoA thiolase (AT); 3-hydroxybutyryl-CoA dehydrogenase (HBD); crotonase (CRT); trans-enoyl-CoA reductase (TER); and alcohol/aldehyde dehydrogenase (AADH).

Introduction

Figure 2:
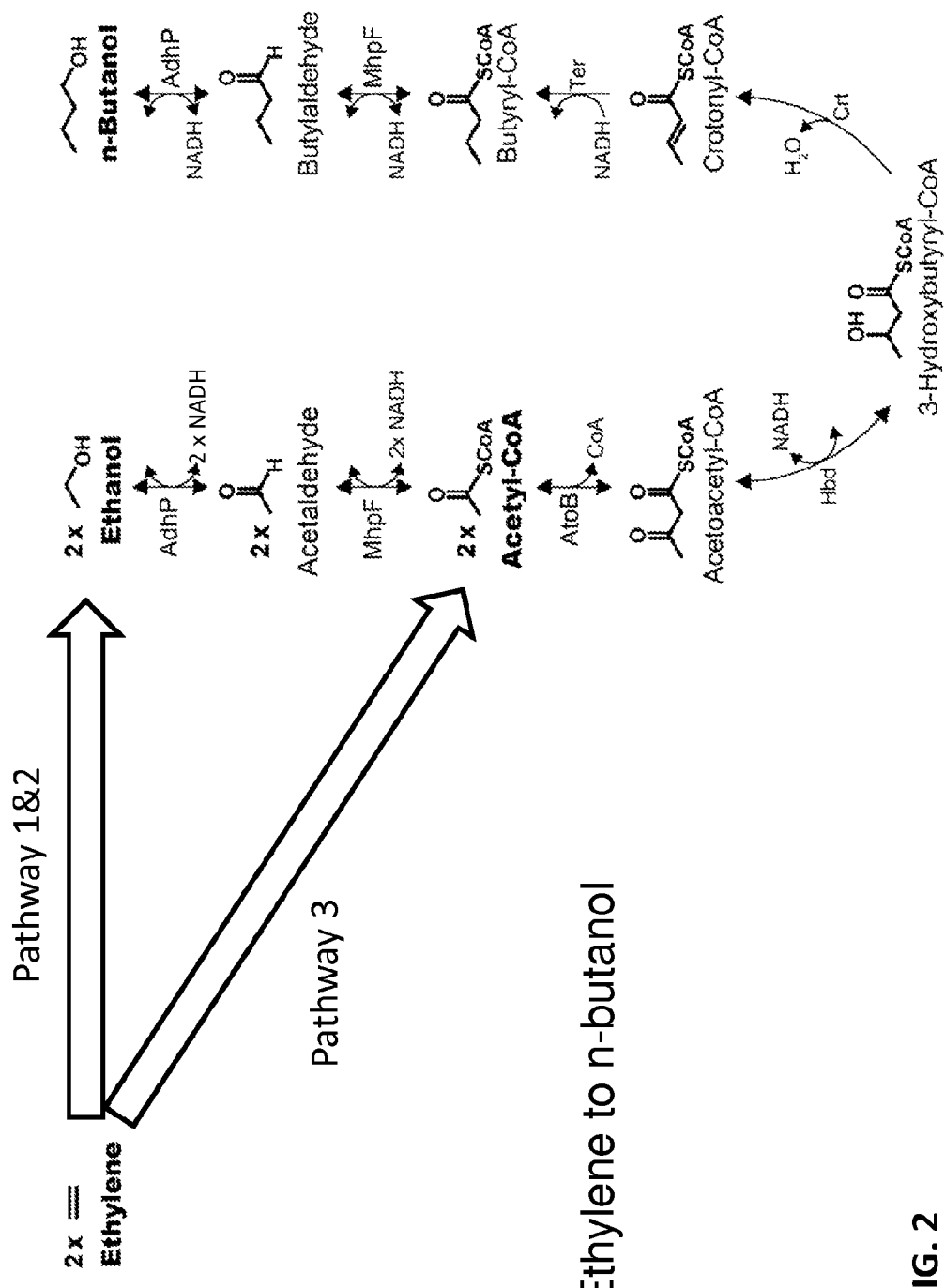
FIG. 2 illustrates the three pathways for the enzymatic production of n-butanol from ethylene.

Described herein are methods for engineering ethylene assimilation pathways into the industrial host *Escherichia coli* to convert ethylene into acetyl-CoA. In order to maximize the chances of a successful transplant into *E. coli* and to optimize efficiency, three alternatives based on engineered enzymes have been used to generate acetyl-CoA (FIG. 1). This acetyl-CoA may be converted into n-butanol through a known enzymatic pathway (FIG. 2).

As shown in FIG. 1, for pathway 1, the initial step is to convert ethylene into ethanol by ethylene hydratase (EH). For pathways 2 and 3, the initial step in the biological assimilation of ethylene is an epoxidation reaction that produces ethylene oxide by alkene monooxygenase. Several alkene monooxygenases from bacteria have been identified (Ginkel et al., *Appl Microbiol Biotechnol* 24, 334-337, 1986; Coleman and Spain, *J Bacteriol* 185, 5536-5545, 2003; Mattes et al., *Arch Microbiol* 183, 95-106, 2005; Perry and Smith, *J Biomol Screen* 11, 553-556, 2006). However, very little characterization of the catalytic properties of this enzyme has been done. These pathways are different from the natural ethylene assimilating pathway in *Nocardioides* sp. strain JS614, which is the only ethylene assimilating pathway identified in nature (Mattes et al., *Arch Microbiol* 183, 95-106, 2005). For Pathway 2, a novel NADH dependent epoxide reductase is used to catalyze the conversion of ethylene oxide to ethanol. The resulting ethanol can readily be converted into n-butanol via acetyl-CoA. In the third pathway, ethylene is converted to acetyl-coA via acetyl-phosphate. The advantage of this pathway is that all of the required enzymes functions exist in nature. Since ethylene assimilation to acetyl-CoA is redox balanced, this pathway may be introduced into *E. coli* without affecting its energy metabolism. From acetyl-CoA, n-butanol can be produced using a pathway known in the art (Atsumi et al., *Metab Eng* 10, 305-311, 2008).

Materials and Methods

Reagents and Bacterial Strains

Restriction enzymes and antarctic phosphatase were from New England Biolabs (Ipswich, Mass., USA). Rapid DNA ligation kit was from Roche (Mannheim, Germany). KOD DNA polymerase was from EMD Chemicals (San Diego, Calif., USA). Oligonucleotides were from Integrated DNA Technologies (San Diego, Calif., USA).

TABLE 1

*E. coli* Strains and Plasmids

| Strain/Plasmid | Description |
| --- | --- |
| BW25113 | rrnBT14 ΔlacZWJ16 hsdR514 ΔaraBADAH33 ΔrhaBADLD78 |
| TG1 | supE hsdΔ5 thiΔ(lac-proAB) F'[traD36 proAB$^+$ lacI$^q$ lacZΔM15] |
| JCL16 | BW25113 F'[traD36 proAB$^+$ lacI$^q$ZΔM15] |
| JCL299 | Same as JCL16 but ΔldhA ΔadhE ΔfrdBC Δpta |
| pEL11 | PLlacO1::atoB$_{Ec}$-adhE2$_{Ca}$-crt$_{Ca}$-hbd$_{Ca}$ ColE1 ori Amp$^r$ |
| pIM8 | PLlacO1::ter$_{Td}$ Cola ori Kan$^r$ |
| pAL812 | PLlacO1:: adhP p15A ori Kan$^r$ |
| pAL811 | PLlacO1:: mhpF p15A ori Kan$^r$ |
| pAL726 | PLlacO1:: mhpF-adhP p15A ori Kan$^r$ |
| pAL727 | PLlacO1:: adhE$_{Ec}$ p15A ori Kan$^r$ |
| pAL728 | PLlacO1:: adhE1$_{Ca}$ p15A ori Kan$^r$ |
| pAL729 | PLlacO1:: adhE2$_{Ca}$ p15A ori Kan$^r$ |
| pAL885 | PLlacO1:: mhpF-mhpE-adhP p15A ori Kan$^r$ |
| pAL881 | PLlacO1:: edgE$_{Lm}$-adhP p15A ori Kan$^r$ |
| pAL896 | PLlacO1:: edgE$_{Lm}$-adhP p15A ori Spec$^r$ |

TABLE 1-continued

E. coli Strains and Plasmids

| Strain/Plasmid | Description |
| --- | --- |
| pBS(Kan)ToMO | Plac:: touABCDEF$_{Ps}$ ColE1 ori Kan$^r$ |
| pAL892 | PLlacO1:: ter$_{Td}$-touABCDEF$_{Ps}$ Cola ori Kan$^r$ |

Ec: from *Escherichia coli*,
Ca; from *Clostridium acetobutylicum*,
Lm: from *Listeria Monocytogenes*,
Lf: *Lysinibacillus fusiformis*.

Cell Culture

For standard culturing purposes, *E. coli* was grown in 5-20 mL of LB media containing any required antibiotics at 37° C. with shaking at 250 rpm in a rotary shaker. For production experiments, *E. coli* was cultured in LB media to an OD$_{600}$ of 0.4, then IPTG (final concentration; 1 mM) was added into the culture to induce enzymes in n-butanol pathway and incubated at 30° C. After 1 h, the culture was spun down, and the supernatant was eliminated. The same volume of M9 media without carbon source as the LB media was added and the cells were resuspended. Consequently, glucose or ethanol was added as a solo carbon source into the culture (the final concentration was 10 g/L each). These cultures were incubated at 30° C. for n-butanol production. OD$_{600}$ and n-butanol concentration of the culture were measured at specific time point(s).

Computational Tools for Protein Design

Computational protein design is a rapidly evolving method for finding proteins with functions not existing in Nature. The use of computational tools allows rapid in silico screening of a vast protein sequence-structure-function space, allowing one to identify a subset of protein sequences likely containing the structure/function of interest. This virtual screening enables one to quickly make large jumps in sequence space and introduce novel function and structure into a protein.

The Rosetta Molecular Modeling Suite has been successfully used for the engineering of many proteins (Schueler-Furman et al., *Science* 310, 638-642, 2005). For example: (1) the design of highly stabilized variants of naturally occurring proteins (Dantas et al., *J Mol Biol* 332, 449-460, 2003; Dantas et al., *J Mol Biol* 366, 1209-1221, 2007; Borgo and Havranek, *Proc Natl Acad Sci USA* 109, 1494-1499, 2012), (2) the design of a protein fold not observed in nature (Kuhlman et al., *Science* 302, 1364-1368, 2003), (3) the specificity redesign and de novo design of protein-protein interactions (Chevalier et al., *Mol Cell* 10, 895-905, 2002); Kortemme et al., *Nat Struct Mol Biol* 11, 371-379, 2004; Joachimiak et al., *J Mol Biol* 361, 195-208, 2006; Fleishman et al., *Science* 332, 816-821, 2011), (4) the design of homing endonucleases with novel specificity (Ashworth et al., *Nature* 441, 656-659, 2006; Thyme et al., *Nature* 461, 1300-1304, 2009), (5) the design of novel enzymes catalyzing chemical reactions for which natural enzymes are not optimized (Zanghellini et al., *Protein Sci* 15, 2785-2794, 2006; Jiang et al., *Science* 319, 1387-1391, 2008; Rothlisberger et al., *Nature* 453, 190-194, 2008; Siegel et al., *Science* 329, 309-313, 2010), and (6) the design of large self-assembling macromolecular structures (King et al., *Science* 336, 1171-1174, 2012). Because the designed protein sequences do not exist in Nature, gene synthesis is central to obtaining the designed protein, and allows one to optimize for expression in any desired host.

The general strategy of computational enzyme design is to use a force field composed of potentials derived empirically (van der Waals interactions, orientation dependent hydrogen bonding, Coulomb electrostatics, and implicit solvation) and statistically (Ramachandran angles, side chain torsions, pair potentials, etc.) to evaluate how substitutions in the protein affect the protein stability and stabilization of the transition state of the desired reaction. Rosetta searches heuristically through combinations of mutations, evaluating the energetics for each set of mutations. It returns the set of mutations determined to be most favorable for both folding and transition state stabilization.

Example 1: Conversion of Ethylene to Ethanol Using Ethylene Hydratase

The wasteful expenditure of energy in the activation O$_2$ for epoxidation of ethylene to ethylene oxide, the branch point for the three originally proposed pathways for conversion of ethylene into n-butanol, can potentially be circumvented by the development of an enzyme that is highly active in the hydration of ethylene directly to ethanol (FIG. 1). Interestingly, very few hydration reactions are carried out on isolated double bonds in biology. Nearly all biological hydration reactions occur on activated alkenes that are conjugated to groups that can resonance stabilize carbanions formed in Michael-type addition reactions.

An important point is that the hydration of ethanol is carried out on a large scale industrially and is responsible for approximately half of the total world production of ethanol annually. The industrial process involves a high temperature gas-phase acid catalyzed hydration reaction and results in a low single-pass yield. The remaining unreacted ethylene is isolated and rerun through the reactor. Given the inefficiency of the current industrial ethylene hydration process, there may well be a substantial market for a high efficiency, low temperature enzyme catalyzed process. Therefore, the methods described herein for the construction of pathways 1 and/or 2 may also be used for ethanol production.

Work on this pathway was initiated by meticulously searching the literature for enzymes that catalyze hydration of isolated, unconjugated double bonds. A thorough search of the literature led to identification of two classes of known alkene hydratases. The first class employs FADH (reduced flavin adenine dinucleotide) as a cofactor. This is mechanistically interesting since the hydration reaction involves no net redox change in the substrate. Two enzymes in this first class that have been investigated are oleate hydratase and 2-haloacrylate hydratase (O'Connell et al., *Bioengineered* 4, 313-321, 2013; Joo et al., *Biochimie* 94, 907-915, 2012; Kim et al., *Appl Microbiol Biotechnol* 95, 929-937, 2012; Bevers et al. *J Bacteriol* 191, 5010-5012, 2009; and Kisic et al., *Lipids* 6, 541-545, 1971). The second class of enzymes is involved in the hydration of terminal alkenes of carotenoids and other natural products. This class includes carotenoid hydratases, kievitone hydratase, and phaseollidin hydratase (Li et al., *Mol Plant Microbe Interact* 8, 388-397, 1995; Turbek et al., *Phytochemistry* 29, 2841-2846, 1990; Turbek et al., *FEMS Microbiol Lett* 73, 187-190, 1992; Sun et al., *Microbiology* 155, 2775-2783, 2009; Steiger et al., *Arch Biochem Biophys* 414, 51-58, 2003).

To date several target enzymes believed to be suitable templates for an ethylene hydratase have been identified. *E. coli* optimized synthetic genes for three (kievitone hydratase, oleate hydratase, and 2-haloacrylate hydratase) have been prepared, and two of these have been cloned (oleate hydratase and 2-haloacrylate hydratase) into the pET28a expression vector. These genes have been sequenced to confirm the correct sequences, transformed into *E. coli*, and shown by SDS-PAGE to yield high level expression of the expected enzymes (data not shown). The specific enzymes investigated are the oleate hydratase (ZP_07049769) from *Lysinibacillus fusiformis*, the 2-haloacrylate hydratase (BAJ13488) from *Pseudomonas* sp. and the kievitone hydratase (AAA87627.1) from *Fusarium solani*, since these are all well expressed in *E. coli* and their activities have been well characterized. Future experiments will purify the oleate and 2-haloacrylate hydratases, assay their activities on their natural substrates to ensure they are fully active, and then test for activity with ethylene and other simple alkenes such as propene and butane.

Example 2: Conversion of Ethylene to Ethanol Using AMO and EOR

The initial step in the biological assimilation of ethylene for pathways 2 and 3 (FIG. 1B) is an epoxidation reaction that produces ethylene oxide by a monooxygenase. In native ethylene utilization pathways, the first enzyme is alkene monooxygenase, AMO (Ginkel et al., *Appl Microbiol Biotechnol* 24, 334-337, 1986; Coleman and Spain, *J Bacteriol* 185, 5536-5545, 2003; Mattes et al., *Arch Microbiol* 183, 95-106, 2005; Perry and Smith, *J Biomol Screen* 11, 553-556, 2006). While several isozymes have been identified, and one heterologously expressed and active in vivo (Perry and Smith, supra, 2006), none have been demonstrated to function in *E. coli*. Therefore, in addition to pursuing AMO, the use of the structurally related toluene monooxygenase (TMO) will also be tested, as well as the functionally related but structurally dissimilar styrene monooxygenase (SMO). Both of these alternative enzymes are well characterized and known to function in *E. coli*. Details discussing each of the three proposed routes to achieve ethylene oxidation are discussed below.

Previous efforts have demonstrated that one potential reason AMO was not functional in *E. coli* was an abundance of rare codons and non-ideal *E. coli* ribosome binding site (RBS) motifs (Smith et al., *Eur J Biochem* 260, 446-452, 1999). In fact, some of the component proteins were not even observed, suggesting that translation was not efficiently occurring. However, the recombinant AMO has been functionally produced in *S. lividans*, showing that if all the AMO components are expressed they can form a functional complex in a heterologous host (Smith et al., supra, 1999). Therefore, the AMO operon will be resynthesized such that both the gene composition and operon structure will be optimized for *E. coli*. *E. coli* optimized genes for each component part will be combined using Gibson assembly (Gibson et al., *Nat Methods* 6, 343-345, 2009) in which an idealized RBS, designed using the RBS calculator (Salis et al., *Nat Biotechnol* 27, 946-950, 2009), will be introduced before each gene. While there are clearly many possible ways to design and assemble the operon, this simple design is likely to at least enable production of each polypeptide to determine if AMO can be functionally produced at any level in *E. coli*. Upon AMO production, the RBS will be further optimized by adjusting gene order and direction, RBS strength, as well as promoter and terminator placements (Temme et al., *Proc Natl Acad Sci USA* 109, 7085-7090, 2012).

While the use of the native AMO gene would be ideal, closely related non-heme diiron enzymes such as methane monooxygenase have never been functionally produced in *E. coli* despite decades of effort (Torres Pazmino et al., *J Biotechnol* 146, 9-24, 2010). However, the enzyme toluene monooxygenase is a closely related non-heme diiron-dependent monooxygenases, sharing the $(\alpha\beta\gamma)_2$ quaternary structure (Small and Ensign, *J Biol Chem* 272, 24913-24920, 1997), and sharing well established functional production in *E. coli* (Pikus et al., *Biochemistry* 35, 9106-9119, 1996; Studts et al., *Protein Expr Purif* 20, 58-65, 2000). Furthermore, toluene monooxygenase has been reported to have rates for alternative substrates, such as 2-butene, on the order of 5 $\mu mol/g_{total\ cell\ protein}/s$ (McClay et al., *Appl Environ Microbiol* 66, 1877-1882, 2000).

While a similar rate for ethylene is expected to be observed, this can likely be improved with enzyme engineering, as TMO has not been naturally evolved to function on ethylene or butene. If rates on ethylene are not greater than 10 $\mu mol/g_{total\ cell\ protein}$'s, two lines of enzyme engineering will be pursued. First, known crystal structures of product or substrate bound TMO (Bailey et al., *Biochemistry* 51, 1101-1113, 2012) will be used to re-engineer the enzyme active site using the computational design techniques described above. In parallel, due to the high structural and functional similarity between TMO and AMO, the recently developed algorithm JANUS, which has been demonstrated to be capable of interconverting enzyme functions (Addington et al., *J Molec Biol*, 425, 1378-1389, 2013), will be used. This is an ideal example of utility of this algorithm in which the aim will be to transfer the reaction specificity of AMO into the structurally and functionally related enzyme TMO.

An alternative to the diiron group of enzymes is a group of flavin-dependent monooxygenases, including styrene monooxygenase, whose X-ray structure has been determined (Ukaegbu et al., *Biochemistry* 49, 1678-1688, 2010). This FAD dependent enzyme has activity on a variety of alkenes including 1-hexene, which is as good as styrene as a substrate (Toda et al., *Appl Microbiol Biotechnol* 96, 407-418, 2012). The kinetics of the enzyme have been investigated in detail (Kantz and Gassner, *Biochemistry* 50, 523-532, 2011). A natural fusion with the FAD reductase component exists, simplifying its application here (Tischler et al., *Appl Biochem Biotechnol* 167, 931-944, 2012). The active site of this enzyme will be engineered to improve specificity for ethylene, and achieving high level expression in *E. coli*.

Figure 3B:
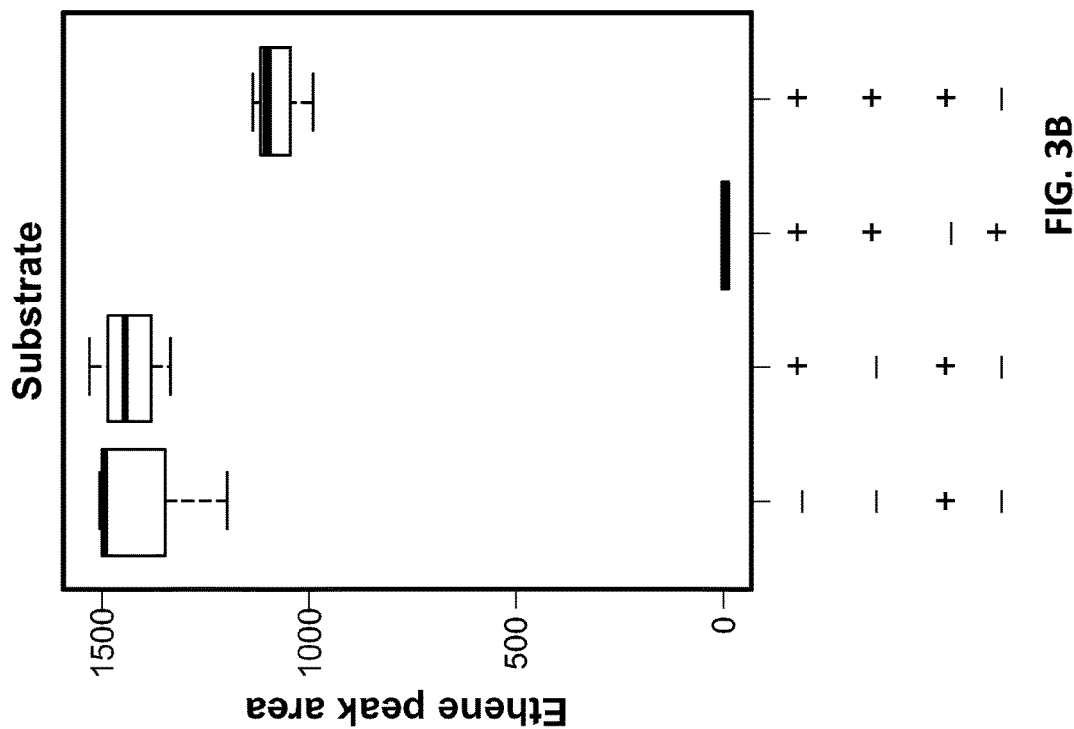
FIG. 3A-B demonstrates the production of oxirane (also known as ethylene oxide) from ethene (the IUPAC name for ethylene) using recombinant bacteria. Oxirane (product) and ethene (substrate) levels are shown after 24 hour incubation. First column: substrate only. Second column: substrate and cells without active enzyme. Third column: no substrate, cells with active enzyme spiked with product. Forth column: substrate and cells with active enzyme, showing substrate depletion and product formation compared to controls.
Figure 3A:
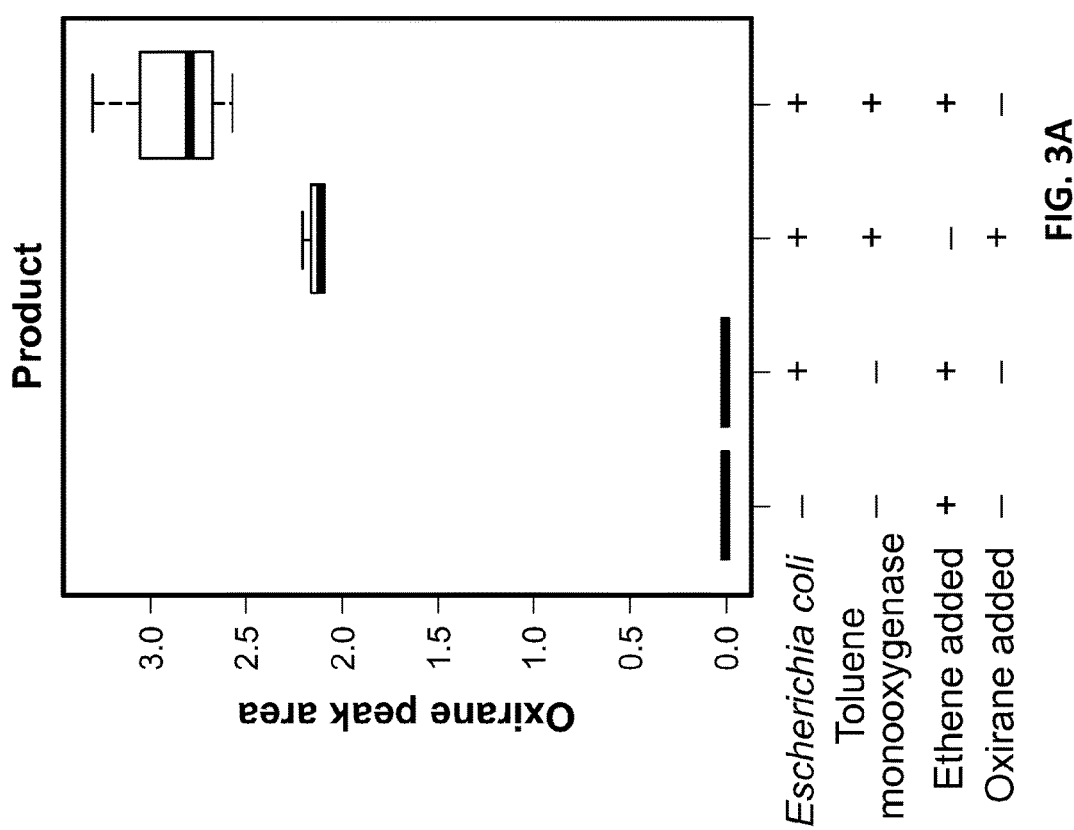

Two toluene monooxygenases (T4MO from *Pseudomonas mendocina*: M65106.1, TOM from *Burkholderia cepacia*: AF349675) were tested for their activities on ethylene. Cell cultures were incubated at 37° C. in a 1.5% ethylene atmosphere. Under these conditions, ethylene is converted into oxirane (ethylene oxide). FIG. 3 demonstrates that toluene monooxygenase activity has been detected in this system using the enzyme T4MO from *Pseudomonas mendocina*: M65106.1.

Several other potential alkene monooxygenases, including an alkene monooxygenase from *Xanthobacter* strain Py2 and an alkene monooxygenase from *Nocardia corallina* B-276, will also be tested. A P450 from *Xanthobacter autotrophius*, an autotrophic organism that grows on ethylene, has been identified and will be tested for ethylene activity (it has been shown to work on halogenated ethenes).

For these pathways, a novel NADH dependent epoxide reductase, EOR, will be designed to catalyze the conversion of ethylene oxide to ethanol. The resulting ethanol will be converted to acetyl-coA by well-characterized ethanol dehydrogenase and acetaldehyde dehydrogenase (FIG. 1). No NADH dependent epoxide reductase is known in nature. The reaction thermodynamics are highly favorable (>10 kcal/mol), and NADH dependent reductases are common. $NAD^+$ dependent formate dehydrogenase will be investigated (Ferry, *FEMS Microbiol Rev* 7, 377-382, 1990), since the active site is similar in size to ethylene oxide, and it is a well-studied enzyme with multiple ligand-bound crystal structures available (Schirwitz et al., *Protein Sci* 16, 1146-1156, 2007; Shabalin et al., *Acta Naturae* 1, 89-93, 2009). In addition, it is a proficient enzyme with specific activities reported to be >7000 µmol/$g_{total\ cell\ protein}$/s (Lu et al., *Appl Microbiol Biotechnol* 86, 255-262, 2010).

A functional search for NAD- and NADP-dependent enzymes revealed about thirty thousand candidates for scaffolds on which to build an enzyme to convert oxirane into ethanol. Filtering out ferridoxin- and metal-dependent enzymes brings the list down to 200. A group of these that may be good candidates as scaffolds for oxirane reductase were compiled (Table 2). Candidates were chosen based on several criteria: 1) catalyzes a simple hydride transfer, 2) no DHFR, 3) metal independent enzymes, and 4) less than 500 amino acids in a monomer. Synthetic genes for these candidates will be tested.

epoxide hydrolase and this is followed by oxidation to glycoaldehyde. The latter will be converted into acetyl-phosphate. The TPP dependent phosphoketolase will be used to convert glycoaldehyde into acetyl-phosphate. TPP dependent enzymes are generally promiscuous and known to react with aldehyde intermediates (Demir et al., *Tetrahedron: Asymmetry* 10, 4769-4774, 1999). Here, the TPP-glycolaldehyde adduct is an intermediate in the cognate reaction. However, it may be necessary to engineer the active site of phosphoketolase to enhance its specificity for glycolaldehyde. This should be readily achievable since the reaction is going from a large to small substrate, and there are numerous crystal structures available (Suzuki et al., *J Biol Chem* 285, 34279-34287, 2010). The resulting acetyl-phosphate will be converted into acetyl-coA by phosphate acetyltransferase.

TABLE 2

| PDB ID | Citation |
|---|---|
| 2AZN | X-RAY Structure of 2,5-diamino-6-ribosylamino-4(3h)-pyrimidinone 5-phosphate reductase |
| 1NNU | Crystal Structure Analysis of *Plasmodium falciparum* enoyl-acyl-carrier-protein reductase with Triclosan Analog |
| 3ORF | Crystal Structure of Dihydropteridine Reductase from *Dictyostelium discoideum* |
| 3RJ5 | Structure of alcohol dehydrogenase from *Drosophila lebanonesis* T114V mutant complexed with NAD+ |
| 1OAA | MOUSE SEPIAPTERIN REDUCTASE COMPLEXED WITH NADP AND OXALOACETATE |
| 2AG8 | NADP complex of Pyrroline-5-carboxylate reductase from *Neisseria meningitidis* |
| 1SNY | Carbonyl reductase Sniffer of *D. melanogaster* |
| 2F1K | Crystal structure of *Synechocystis* arogenate dehydrogenase |
| 2G5C | Crystal Structure of Prephenate Dehydrogenase from *Aquifex aeolicus* |
| 3JYO | Quinate dehydrogenase from *Corynebacterium glutamicum* in complex with NAD |
| 1LUA | Structure of methylene-tetrahydromethanopterin dehydrogenase from *Methylobacterium extorquens* AM1 complexed with NADP |
| 1LC3 | Crystal Structure of a Biliverdin Reductase Enzyme-Cofactor Complex |
| 1YJQ | Crystal structure of ketopantoate reductase in complex with NADP+ |
| 3ZHB | R-imine reductase from *Streptomyces kanamyceticus* in complex with NADP. |
| 3AJR | Crystal structure of L-3-Hydroxynorvaline bound L-Threonine dehydrogenase (Y137F) from Hyperthermophilic Archaeon *Thermoplasma volcanium* |
| 1EE9 | CRYSTAL STRUCTURE OF THE NAD-DEPENDENT 5,10-METHYLENETETRAHYDROFOLATE DEHYDROGENASE FROM *SACCHAROMYCES CEREVISIAE* COMPLEXED WITH NAD |
| 1E6U | GDP 4-KETO-6-DEOXY-D-MANNOSE EPIMERASE REDUCTASE |
| 2DBQ | Crystal Structure of Glyoxylate Reductase (PH0597) from *Pyrococcus horikoshii* OT3, Complexed with NADP (I41) |
| 3KVO | Crystal structure of the catalytic domain of human Hydroxysteroid dehydrogenase like 2 (HSDL2) |
| 2I3G | Crystal structure of N-Acetyl-gamma-Glutamyl-Phosphate Reductase (Rv1652) from *Mycobacterium tuberculosis* in complex with NADP+. |
| 2ZB4 | Crystal structure of human 15-ketoprostaglandin delta-13-reductase in complex with NADP and 15-keto-PGE2 |
| 2V6G | STRUCTURE OF PROGESTERONE 5BETA-REDUCTASE FROM *DIGITALIS LANATA* IN COMPLEX WITH NADP |
| 3PZR | Crystals structure of aspartate beta-Semialdehyde dehydrogenase from *Vibrio Cholerae* with NADP and product of S-carbamoyl-L-cysteine |
| 1O2D | Crystal structure of Alcohol dehydrogenase, iron-containing (TM0920) from *Thermotoga maritima* at 1.30 A resolution |
| 2D2I | Crystal Structure of NADP-Dependent Glyceraldehyde-3-Phosphate Dehydrogenase from *Synechococcus* Sp. complexed with Nadp+ |
| 3OET | D-Erythronate-4-Phosphate Dehydrogenase complexed with NAD |
| 1KOL | Crystal structure of formaldehyde dehydrogenase |
| 1VLJ | Crystal structure of NADH-dependent butanol dehydrogenase A (TM0820) from *Thermotoga maritima* at 1.78 A resolution |
| 1L18 | Crystal structure of mannitol dehydrogenase in complex with NAD |

Example 3: Conversion of Ethylene to Acetyl-CoA Through Ethylene Glycol

In the third pathway, ethylene is converted to acetyl-coA via acetyl-phosphate (FIG. 1). The advantages of this pathway are that no cofactor biosynthetic pathways need to be introduced and all required enzymes exist in nature. Ethylene oxide will be first converted into ethylene glycol by Example 4: Construction of the Ethanol Assimilation Pathway In order to generate n-butanol from the ethanol produced as described above, the synthetic n-butanol pathway described in Atsumi et al., *Metab Eng* 10, 305-311, 2008 and Shen et al., *Appl Environ Microbiol* 77, 2905-2915, 2011 will be combined with pathways 1, 2, and 3 (FIG. 1).

The E. coli strain with this pathway produced more than 30 g/L n-butanol with 88% theoretical yield. In this pathway, two molecules of acetyl-CoA are condensed into acetoacetyl-CoA by an acetoacetyl-CoA thiolase (AtoB (E. coli)). The acetoacetyl-CoA is reduced to 3-hydroxybutyryl-CoA by an NADH-dependent 3-hydroxybutyryl-CoA dehydrogenase (Hbd (C. acetobutylicum)). A crotonase (Crt (C. acetobutylicum)) then catalyzes a dehydration to yield crotonyl-CoA (Waterson et al., *J Biol Chem* 247, 5266-5271, 1972). A trans-enoyl-CoA reductase (Ter (*Treponema denticola*)) reduces crotonyl-CoA to butyryl-CoA (Tucci and Martin, *FEBS Lett* 581, 1561-1566, 2007). Lastly, butyryl-CoA is sequentially reduced by a single NADH-dependent aldehyde/alcohol dehydrogenase (AdhE2) to n-butanol (Atsumi et al., *Metab Eng* 10, 305-311, 2008).

The production of n-butanol from ethanol in the n-butanol-producing strain described in Shen et al., *Appl Environ Microbiol* 77, 2905-2915, 2011 was attempted. The strain was grown in LB media to an $OD_{600}$ of 0.4, then IPTG (final concentration; 1 mM) was added into the culture to induce enzymes in n-butanol pathway and incubated at 30° C. After 1 h, the culture was span down and the supernatant was eliminated. The same volume of M9 media without carbon source as the LB media was added and the cells were resuspended. Consequently, glucose or ethanol was added as a solo carbon source into the culture (the final concentration was 10 g/L each). These cultures were incubated at 30° C. for n-butanol production. $OD_{600}$ and n-butanol concentration of the culture were measured at specific time points.

Figure 4A:
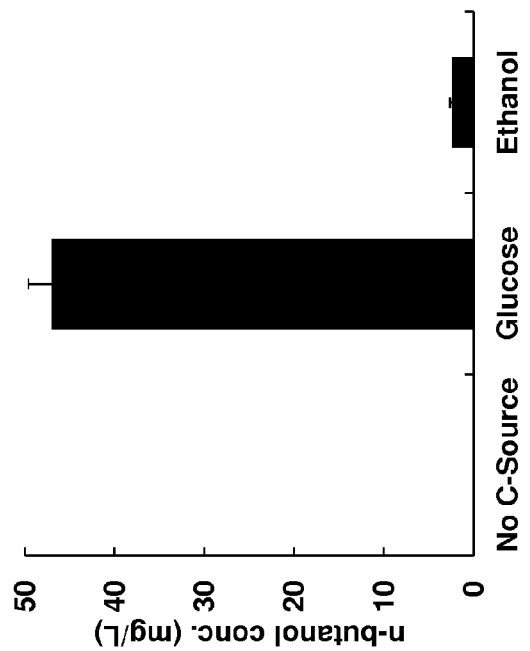
FIG. 4A-B shows the cell density and n-butanol titer produced by an n-butanol-producing strain.

As shown in FIG. 4A, the cell density in not only M9-glucose media but also M9-ethanol media was found to increase. As AdhE2 in the n-butanol pathway has ability to convert ethanol to acetyl-CoA, the strain could assimilate ethanol using AdhE2 to grow.

Figure 4B:
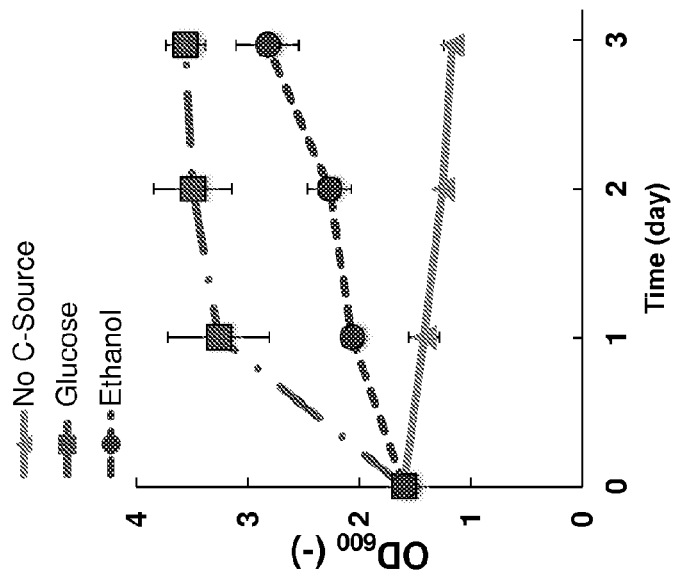

FIG. 4B shows that the strain produced 2.4 mg/L n-butanol in M9-ethanol media in 3 days. However, the titer was about 20-times less than in M9-glucose. This result indicated that improving ethanol assimilating ability is necessary to improve n-butanol production from ethanol.

Although *E. coli* encodes the genes constituting ethanol assimilation pathway, ethanol is not metabolized in wild type *E. coli* at a sufficient rate to support growth. Certain mutant strains, however, with altered pattern of gene expression can grow on ethanol as a carbon and energy source. These findings mean that conversion of ethanol to acetyl-CoA is not efficient in *E. coli*. To acquire high n-butanol productivity, the conversion efficiency of ethanol to acetyl-CoA has to be improved. Acetyl-CoA is one of the most important metabolite for *E. coli* to grow. Ethanol conversion efficiency can be estimated by growth of *E. coli*.

Genes functioning in the ethanol assimilating pathway in *E. coli* were screened. Two different ethanol assimilating pathways were constructed using genes from *E. coli* and compared. The first pathway consists of two enzymes: AdhP (ECK1472) and MhpF (ECK0348). AdhP converts ethanol to acetoaldehyde, and then the acetoaldehyde is converted to acetyl-CoA by MhpF. The second pathway is based on only one enzyme: AdhE (ECK1235). AdhE is able to catalyze the reactions catalyzed by both AdhP and MhpF.

Figure 5A:
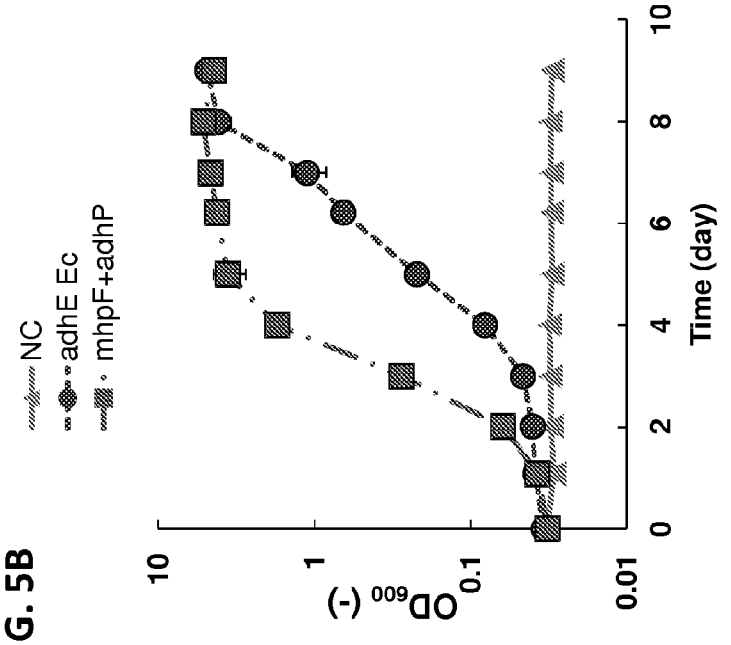
FIG. 5A-B shows the growth rate for *E. coli* overexpressing MhpF and AdhP (dashed lines) or AdhE (dotted and dashed lines), compared to wild-type *E. coli* (NC), when using glucose or ethanol as the carbon source.
Figure 5B:
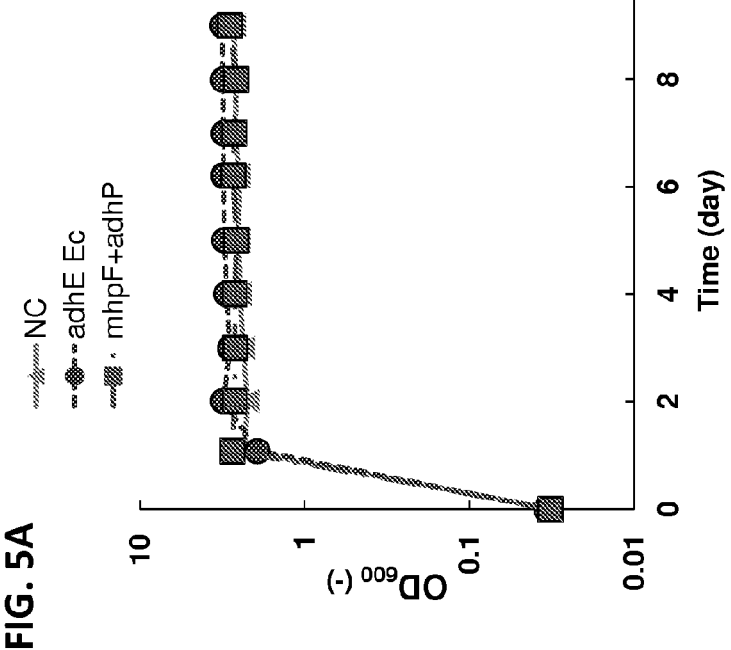

To compare these two pathways, strains overexpressing AdhP and MhpF or AdhE were inoculated in M9 minimal media with either glucose or ethanol as the sole carbon source. FIG. 5 shows the growth rate of these strains. In M9-glucose media, these strains showed almost same in growth rate (FIG. 5A). On the other hand, growth rates of these strains were significantly different in M9-ethanol media (FIG. 5B). The control strain without ethanol assimilating pathway was not able to grow in M9-ethanol. The AdhE-overexpressing strain (AdhE strain) and MhpF/AdhP-overexpressing strain (MhpF/AdhP strain) could grow much better than control strain, but the MhpF/AdhP strain grew faster than the AdhE strain.

TABLE 3

Screening Genes for Ethanol Assimilation

| Genes | Growth rate in ethanol ($h^{-1}$) |
|---|---|
| mRFP1 | 0.456 ± 0.014 (in Glucose) |
| adhP | 0.026 ± 0.001 |
| mhpF | — |
| mhpF-adhP | 0.067 ± 0.005 |
| adhE | 0.041 ± 0.003 |
| adhE1* | — |
| adhE2* | 0.054 ± 0.005 |
| mhpFE-adhP | 0.071 ± 0.001 |
| edgE†-adhP | 0.167 ± 0.002 |

—: no growth,
*gene from *Clostridium acetobutylicum*,
†*Listeria monocytogenes*

To further improve the ethanol assimilating pathway, enzymes involved in ethanol assimilation were screened (Table 3). Genes or combinations of genes were expressed in *E. coli*, and growth rate of the strains in M9-ethanol was measured. As shown in Table 3, EdgE and AdhP was best combination. EdgE is from *Listeria monocytogenes* and catalyzes reaction from acetaldehyde to acetyl-CoA. The growth rate of the strain expressing EdgE and AdhP with ethanol was about 40% of growth rate with glucose.

Example 5: Production of n-Butanol Using Ethanol Assimilation Pathways

The above results demonstrate that EdgE and AdhP may be used as an efficient ethanol assimilation pathway. EdgE and AdhP were introduced into an n-butanol-producing strain to produce n-butanol from ethanol. The strains were grown in LB media to an $OD_{600}$ of 0.4, then IPTG (final concentration; 1 mM) was added into the culture and incubated at 37° C. After 4 h, the culture was span down and the supernatant was eliminated. The same volume of M9 media without carbon source as the LB media was added and the cells were resuspended. Glucose or ethanol was added as a solo carbon source into the culture (the final concentration is 10 g/L each). These cultures were incubated at 37° C. for 24 h. Consequently, n-butanol concentration in the cultures was measured.

Figure 6:
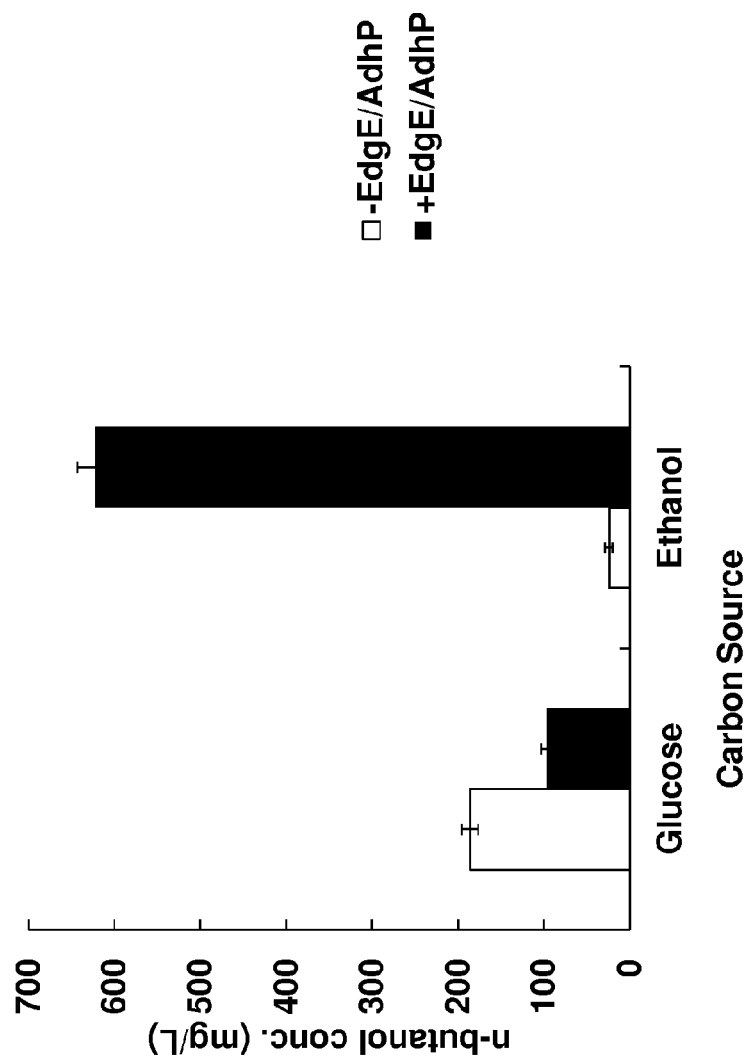
FIG. 6 shows that expression of EdgE and AdhP greatly enhances the production of n-butanol from an n-butanol-producing strain grown in media containing ethanol. EdgE and AdhP were expressed in the n-butanol pathway as an ethanol assimilating pathway. The strains were incubated at 37° C. for 24 h to produce n-butanol.

As shown in FIG. 6, In M9-glucose media, an n-butanol-producing strain expressing EdgE/AdhP (+EdgE/AdhP strain) produced 97 mg/L of n-butanol in 24 h. This titer was about half amount of n-butanol that n-butanol strain without EdgE/AdhP (−EdgE/AdhP strain) produced (186 mg/L). As +EdgE/AdhP strain produce more ethanol (data not shown), the n-butanol production in the strain reduced. In M9-ethanol, on the other hand, 622 mg/L or 24 mg/L of n-butanol was produced in +EdgE/AdhP strain or −EdgE/AdhP strain, respectively.

Importantly, the +EdgE/AdhP strain produced about 25-times more n-butanol than the −EdgE/AdhP strain. In addition, the titer of n-butanol in +EdgE/AdhP strain with ethanol was 3-times higher than in −EdgE/AdhP with glucose. These results indicate that the novel ethanol-to-n-butanol pathway described herein is more effective than a glucose-to-n-butanol pathway for the production of n-butanol.

Example 6: Characterization of Ethylene Hydratase Enzymes

Figure 7:
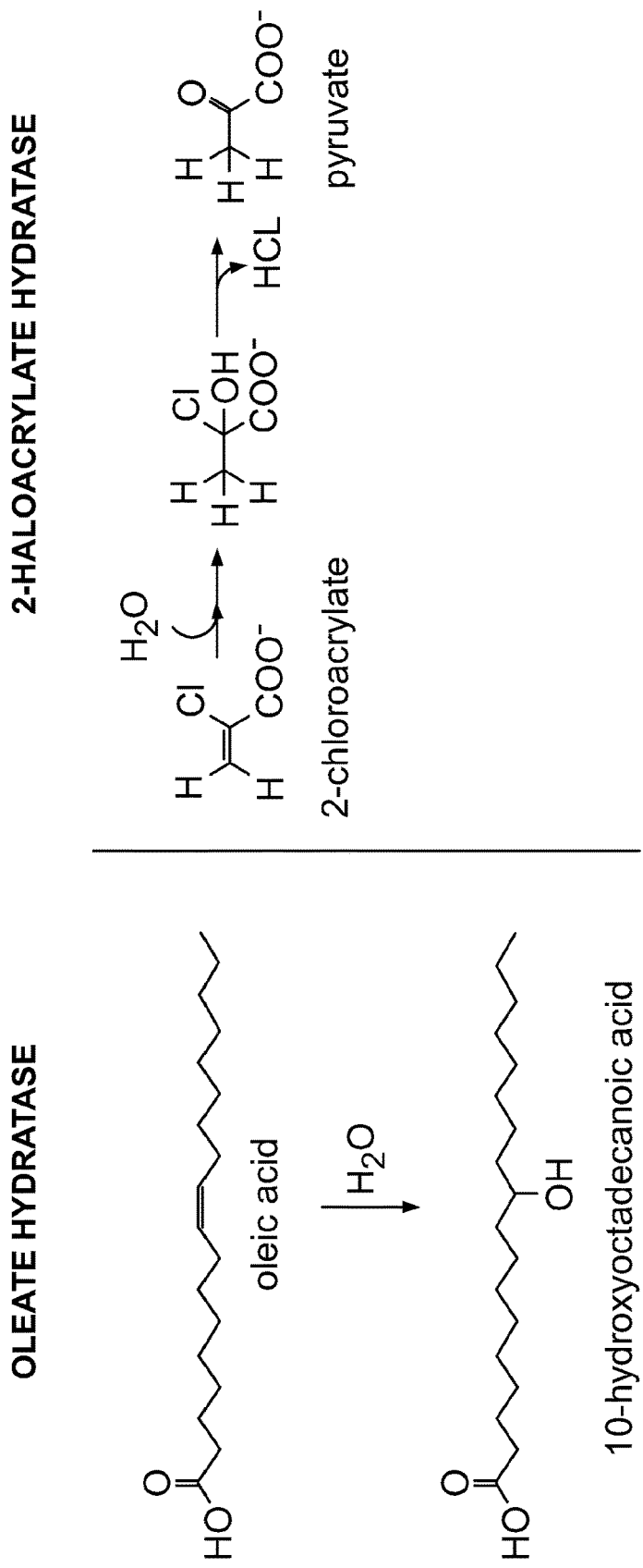
FIG. 7 shows the wild-type (e.g., endogenous) reactions catalyzed by oleate hydratase and 2-chloroacrylate hydratase.

As described in Example 1, *E. coli* optimized synthetic genes for oleate hydratase and 2-haloacrylate hydratase have been cloned into the pET28a expression vector. These genes have been sequenced to confirm the correct sequences, transformed into *E. coli*, and shown by SDS-PAGE to yield high level expression of the expected enzymes. The specific enzymes investigated are the oleate hydratase (ZP_07049769) from *Lysinibacillus fusiformis* and the 2-haloacrylate hydratase (BAJ13488) from *Pseudomonas* sp. As discussed above, oleate hydratase enzymes catalyze the conversion of oleate and water to (R)-10-hydroxystearate, also known as 10-hydroxyoctadecanoic acid (EC 4.2.1.53), whereas 2-haloacrylate hydratase enzymes catalyze the conversion of 2-chloroacrylate to pyruvate using $FADH_2$ as a co-factor (FIG. 7).

In order to characterize the activities of these two enzymes in converting ethylene to ethanol (see "Pathway 1" in FIG. 1), optimized GC-FID methods were used. For oleate hydratase activity, 50 µg purified oleate hydratase was mixed in a reaction with 50 mM PIPES buffer (pH 6.5), 0.1 mM FAD, 1 mM $Na_2S_2O_4$, 5 mM octanoic acid, and water up to 1 mL. For 2-haloacrylate hydratase activity, 50 µg purified 2-haloacrylate hydratase was mixed in a reaction with 50 mM PIPES buffer (pH 6.5), 0.1 mM FAD, 1 mM $Na_2S_2O_4$, and water up to 1 mL. After introducing 99% ethylene gas into each reaction for 30 seconds, the reactions were incubated for 72 hours, then heated to 75° C. for 1 minute. 10 µL of the vial headspace from each reaction was then injected onto the GC-FID.

Figure 8:
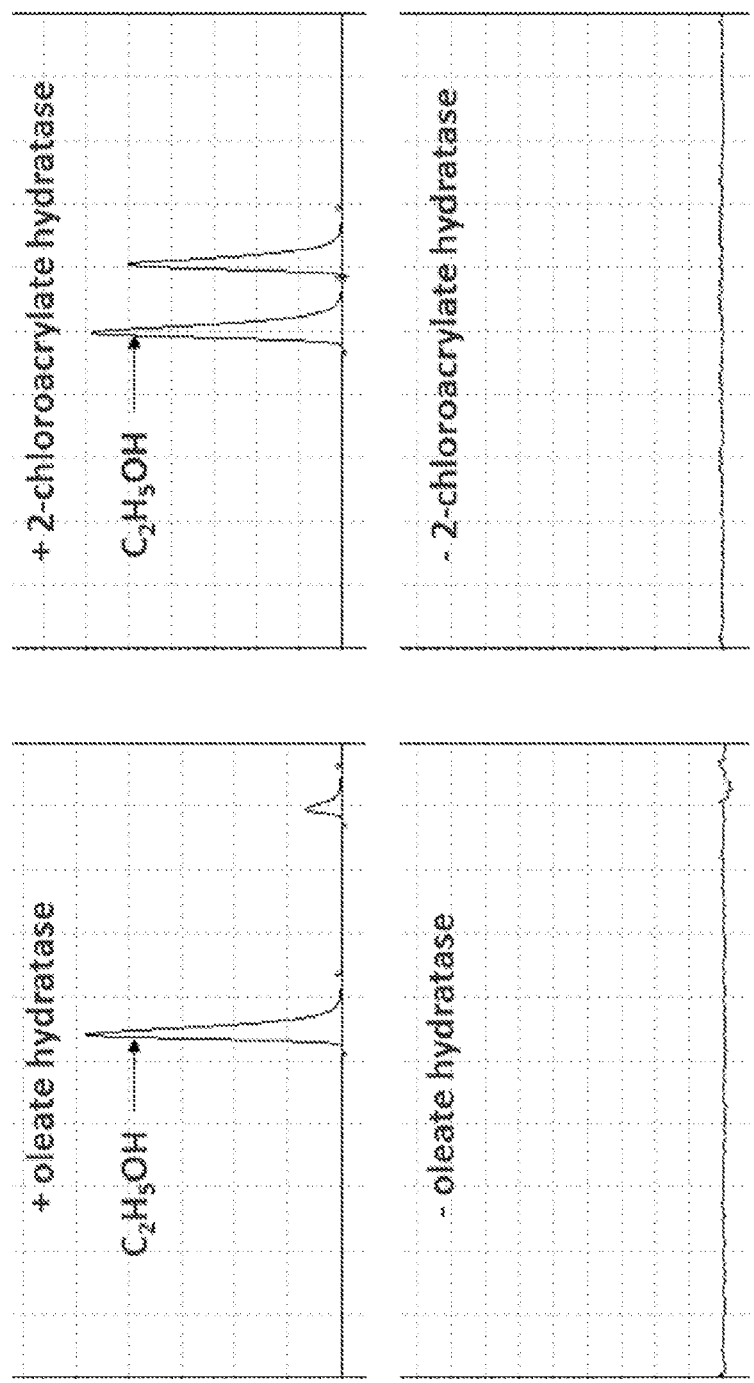
FIG. 8 shows the Gas Chromatography-Flame Ionization Detector (GC-FID) analysis of reactions with ethylene gas and purified oleate hydratase or 2-chloroacrylate hydratase.

As shown in FIG. 8, both oleate hydratase and 2-haloacrylate hydratase produced ethanol from ethylene, as detected by the presence of ethanol in a vial headspace. No ethanol was detected for either reaction in the absence of enzyme. These results demonstrate the successful conversion of ethylene to ethanol using oleate hydratase and 2-haloacrylate hydratase.

We claim:

1. An *Escherichia coli* bacterium transformed with a heterologous polynucleotide encoding a toluene monooxygenase (TOM) from *Pseudomonas mendocina* or *Burkholderia cepacia* and utilizing an endogenous ethylene oxide reductase (EOR), wherein heterologous expression of the TOM and endogenous expression of the EOR results in an increase in production of ethanol as compared to a corresponding bacterium lacking the heterologous polynucleotide.

2. The bacterium of claim 1, wherein the toluene monooxygenase is a *Pseudomonas mendocina* toluene monooxygenase.

3. The bacterium of claim 1, wherein the toluene monooxygenase is a *Burkholderia cepacia* toluene monooxygenase.

4. The bacterium of claim 1, wherein the EOR is an $NAD^+$ dependent formate dehydrogenase.

5. A method for producing ethanol, the method comprising:
   a) providing the bacterium of claim 1; and
   b) culturing the bacterium of (a) in culture medium comprising a substrate under conditions suitable for the conversion of the substrate to ethanol,
   wherein the substrate comprises one or both of ethylene and glucose, and wherein expression of the TOM and the EOR results in an increase in production of ethanol as compared to a corresponding bacterium lacking the heterologous polynucleotide, when cultured under the same conditions.

6. The method of claim 5, further comprising step (c) substantially purifying the ethanol.

7. The bacterium of claim 1, wherein the bacterium further comprises a further recombinant polynucleotide encoding an alcohol/aldehyde dehydrogenase (AADH), wherein expression of the TMO and the EOR, in combination with the AADH results in an increase in production of acetyl-CoA as compared to a corresponding bacterium lacking the heterologous and recombinant polynucleotides.

8. The bacterium of claim 7, wherein the AADH is an *E. coli* AdhE.

9. The bacterium of claim 1, wherein the bacterium further comprises a recombinant polynucleotide encoding an ethanol dehydrogenase (EDH), wherein expression of the TOM and the EOR, in combination with the EDH results in an increase in production of an acetaldehyde as compared to a corresponding bacterium lacking the heterologous and recombinant polynucleotides.

10. The bacterium of claim 9, wherein the EDH is an *E. coli* AdhP.

11. The bacterium of claim 9, wherein the bacterium further comprises a further recombinant polynucleotide encoding an acetoaldehyde dehydrogenase (ALDH), wherein expression of the TOM and the EOR, in combination with the EDH and the ALDH results in an increase in production of acetyl-CoA as compared to a corresponding bacterium lacking the heterologous and recombinant polynucleotides.

12. The bacterium of claim 11, wherein the ALDH is an *E. coli* MhpF.

13. The bacterium of claim 11, wherein the ALDH is a *Listeria monocytogenes* EdgE.

14. The bacterium of claim 13, wherein the EDH is an *E. coli* AdhP.

15. The bacterium of claim 1, wherein the heterologous polynucleotide is stably integrated into the genome of the bacterium.

* * * * *